(12) United States Patent
Bonner et al.

(10) Patent No.: US 7,695,752 B2
(45) Date of Patent: Apr. 13, 2010

(54) TARGET ACTIVATED MICROTRANSFER

(75) Inventors: Robert F. Bonner, Washington, DC (US); Thomas J. Pohida, Monrovia, MD (US); Michael R. Emmert-Buck, Easton, MD (US); Michael Anthony Tangrea, Odenton, MD (US); Rodrigo F. Chuaqui, North Potomac, MD (US)

(73) Assignee: The Government of the United States of America as represented by the Secretary of the Department of Health and Human Services, Washington, DC (US)

( * ) Notice: Subject to any disclaimer, the term of this patent is extended or adjusted under 35 U.S.C. 154(b) by 364 days.

(21) Appl. No.: 11/202,848

(22) Filed: Aug. 12, 2005

(65) Prior Publication Data

US 2006/0172278 A1    Aug. 3, 2006

Related U.S. Application Data

(63) Continuation-in-part of application No. 10/543,218, filed as application No. PCT/US03/023317 on Jul. 23, 2003.

(60) Provisional application No. 60/442,399, filed on Jan. 24, 2003.

(51) Int. Cl.
    *B05D 1/00* (2006.01)
(52) U.S. Cl. ............... 427/2.13; 427/2.11; 427/464; 435/283.1; 435/287.3; 356/36; 356/38; 356/428; 428/346
(58) Field of Classification Search ............. 428/346; 427/2.11; 356/36; 435/1.1, 29
See application file for complete search history.

(56) References Cited

U.S. PATENT DOCUMENTS 4,016,043 A    4/1977    Schuurs et al.

(Continued)

FOREIGN PATENT DOCUMENTS

WO    WO 97/13838    4/1997

(Continued)

OTHER PUBLICATIONS

"Alkaline Phosphatase Substrate-Chromogen (BCIP/NBT) Kit," Biomeda, http://www.biomeda.com/site/cat/S04/specsheet.html, 2 pages, visited Oct. 21, 2002.

(Continued)

*Primary Examiner*—Nelson Yang
(74) *Attorney, Agent, or Firm*—Klarquist Sparkman, LLP

(57) ABSTRACT

A device for performing target activated transfer that includes a mounting surface for mounting a tissue sample; and a light source positioned to substantially uniformly irradiate both stained and unstained regions of the tissue sample with light energy that activates the reagent to selectively adhere the stained regions to a transfer surface. Also described is an automated system for transferring tissue from a tissue sample to a transfer substrate. The system includes means for holding a tissue section that includes targets specifically stained with an absorptive stain thereby resulting in a stained tissue surface, and a flexible transfer film that includes a lower thermoplastic layer in sufficient thermal contact with the stained tissue surface; an irradiating assembly configured to provide a predetermined uniform light dose to the entire tissue section; and means for applying a constant pressure to the transfer film during irradiation.

28 Claims, 11 Drawing Sheets

U.S. PATENT DOCUMENTS

| | | | |
|---|---|---|---|
| 4,232,119 | A | 11/1980 | Carlsson et al. |
| 4,889,818 | A | 12/1989 | Gelfand et al. |
| 4,943,531 | A | 7/1990 | Goff et al. |
| 5,021,335 | A | 6/1991 | Tecott et al. |
| 5,091,301 | A | 2/1992 | Zuerner |
| 5,109,124 | A | 4/1992 | Ramachandran et al. |
| 5,168,038 | A | 12/1992 | Tecott et al. |
| 5,169,939 | A | 12/1992 | Gefter et al. |
| 5,200,270 | A | 4/1993 | Ishida et al. |
| 5,252,457 | A | 10/1993 | Snodgrass et al. |
| 5,294,535 | A | 3/1994 | Gribnau et al. |
| 5,465,151 | A | 11/1995 | Wybourne et al. |
| 5,506,105 | A | 4/1996 | Haydock |
| 5,514,545 | A | 5/1996 | Eberwine |
| 5,589,333 | A | 12/1996 | Bagasra et al. |
| 5,597,692 | A | 1/1997 | Coghlan et al. |
| 5,643,721 | A | 7/1997 | Spring et al. |
| 5,665,539 | A | 9/1997 | Sano et al. |
| 5,705,158 | A | 1/1998 | Hansen et al. |
| 5,731,146 | A | 3/1998 | Duck et al. |
| 5,770,458 | A | 6/1998 | Klimov et al. |
| 5,843,640 | A | 12/1998 | Patterson et al. |
| 5,843,644 | A | 12/1998 | Liotta et al. |
| 5,843,657 | A | 12/1998 | Liotta et al. |
| 5,846,438 | A | 12/1998 | Pall et al. |
| 5,846,814 | A | 12/1998 | Galla et al. |
| 5,972,721 | A | 10/1999 | Bruno et al. |
| 5,998,588 | A | 12/1999 | Hoffman et al. |
| 6,010,888 | A | 1/2000 | Liotta et al. |
| 6,074,869 | A | 6/2000 | Pall et al. |
| 6,087,134 | A | 7/2000 | Saunders |
| 6,132,722 | A | 10/2000 | Siemers et al. |
| 6,183,995 | B1 | 2/2001 | Burmer et al. |
| 6,187,567 | B1 | 2/2001 | Li et al. |
| 6,194,157 | B1 | 2/2001 | Tsuchiya et al. |
| 6,204,030 | B1 | 3/2001 | Liotta et al. |
| 6,242,503 | B1 | 6/2001 | Kozma et al. |
| 6,251,467 | B1 | 6/2001 | Liotta et al. |
| 6,251,516 | B1 | 6/2001 | Bonner et al. |
| 6,261,789 | B1 | 7/2001 | Reiter et al. |
| 6,300,317 | B1 | 10/2001 | Szoka, Jr. et al. |
| 6,613,564 | B2 | 9/2003 | Ohbayashi et al. |
| 6,690,470 | B1 | 2/2004 | Baer et al. |
| 2001/0005586 | A1 | 6/2001 | Palsson et al. |
| 2001/0028934 | A1 | 10/2001 | Baer et al. |
| 2001/0031481 | A1 | 10/2001 | Liotta et al. |
| 2001/0041336 | A1 | 11/2001 | Anderson et al. |
| 2002/0019046 | A1 | 2/2002 | Carpenter et al. |
| 2002/0045160 | A1 | 4/2002 | Carrion et al. |
| 2002/0094533 | A1 | 7/2002 | Hess et al. |
| 2002/0155496 | A1 | 10/2002 | Charles et al. |
| 2005/0176068 | A1 | 8/2005 | Emmert-Buck et al. |
| 2006/0134692 | A1 | 6/2006 | Emmert-Buck et al. |

FOREIGN PATENT DOCUMENTS

| | | |
|---|---|---|
| WO | WO 00/017390 | 3/2000 |
| WO | WO 00/49410 | 8/2000 |
| WO | WO 01/33190 | 5/2001 |
| WO | WO 01/40454 | 6/2001 |
| WO | WO 02/10751 A2 | 2/2002 |
| WO | WO 03/090780 | 11/2003 |
| WO | WO 2004/068104 A2 | 8/2004 |

OTHER PUBLICATIONS

"Arcturus Announces the Introduction of its PixCell® IIe Laser Capture Microdissection System," Arcturus, http://www.arctur.com/about/news/news_pixcelliie.htm, 1 page, visited Sep. 21, 2004.

"Arcturus Introduces the AutoPix™ Automated Laser Capture Microdissection System," Arcturus, http://www.arctur.com/about/new/news_autopix_lcm_system.htm, 2 pages, visited Sep. 21, 2004.

"Arcturus' PixCell a Finalist for Technological Innovation Award in Medical Diagnostics," Arcturus, http://www.arctur.com/about/news/news_discover.htm, 1 page, visited Sep. 21, 2004.

"Background (NIH)," Laser Capture Microdissection LCM Facility, University of Chicago, http://lcm.bsd.uchicago.edu/background.htm, 2 pages, visited Aug. 20, 2002.

Bonner et al., "Laser capture microdissection: molecular analysis of tissue," *Science* 278(5342):1481, 1483, 1997.

"CapSure® LCM Caps—Precision-designed for Optimal Microdissection," Arcturus, http://www.arctur.com/lab_portal/products/_capsure_main.htm, 2 pages, visited Sep. 21, 2004.

"CapSure® Macro LCM Caps—Extract Large Amounts of Cells," Acturus, http://www.arctur.com/lab_portal/products/capsure_macro.htm, 2 pages, visited Sep. 21, 2004.

Chuaqui et al., "Post-analysis follow-up and validation of microarray experiments," *Nature Genetics Supplement* 32:509-514, Dec. 2002.

"Clonis™ microengineering and sorting cells in culture and microdissecting tissues," Bio-Rad Laboratories, 6 pages, May 20, 2002.

Connolly et al., "A new monoclonal antibody, P2A8(6), that specifically recognizes a novel epitope on the multidrug resistance-associated protein 1 (MRP1), but not on MRP2 nor MRP3," PubMed (cited from *Hybrid Hybridomics* 2001;20(5-6)333-41), 1 page, visited Sep. 25, 2002.

Emmert-Buck et al., "Laser capture microdissection," *Science* 274:998-1001, 1996.

"Ethylene-Vinyl Acetate Copolymer (EVA)," *The Loctite Design Guide for Bonding Rubbers and TPEs*, http://216.239.35.100/search?q=cache:gmpJqH8EYEC:www.loctite.com/pdf/pg24-25.pdf..., 3 pages, visited Aug. 18, 2002.

*Federal Register, Notices* 67(141):48195-48196, Jul. 23, 2002.

Fend et al., "Technical Advance, Immuno-LCM: laser capture microdissection of immunostained frozen sections for mRNA analysis," *American Journal of Pathology* 154(1):61-66, 1999.

Harris et al., "Efficient generation of monoclonal antibodies for specific protein domains using recombinant immunoglobulin fusion proteins: pitfalls and solutions," PubMed (cited from *J Immunol Methods* Oct. 15, 2002;268(2):245), 1 page, visited Sep. 25, 2002.

Huang, "Microdissection and Laser Capture Micromanipulation," National Institute of Child Health & Human Development, http://www.nichd.nih.gov/autism/abstracts/huang.htm, 2 pages, visited Sep. 21, 2004.

International Search Report from International Application No. PCT/US2003/023317.

Kamalesh et al., "Biocompatability of electroactive polymers in tissues," PubMed (cited from *J Biomed. Mater Res* Dec. 5, 2000;52(3):467-78), 1 page, visited Aug. 18, 2002.

"Laser Capture Microdissection from NIH/Arcturus Engineering, Inc.," http://www.ibms.sinica.edu.tw/htlm/public1-b3-3.htm, 3 pages, visited Aug. 20, 2002.

Mojsilovic-Petrovic et al., "Development of rapid staining protocols for laser-capture microdissection of brain vessels from human and rat coupled to gene expression analyses," *Journal of Neuroscience Methods* 133:39-48, 2004.

Murakami et al., "IF-LCM: laser capture microdissection of immunofluorescently defined cells for mRNA analysis *rapid communication*," *Kidney International* 58:1346-1353, 2000.

Paragas et al., "The ELF-97 phosphatase substrate provides a sensitive, photostable method for labelling cytological targets," PubMed (cited from *J Microsc* May 2002;206(Pt2):106-19, 1 page, visited Aug. 18, 2002.

"PixCell® IIe Laser Capture Microdissection (LCM) Instrument—Engineered for Speed and Convenience," Arcturus, http://www.arctur.com/lab_portal/products/pixcell_speed_convenience.htm, 3 pages, visited Sep. 21, 2004.

"PixCell® IIe Laser Capture Microdissection (LCM) Instrument—Fluorescence Package," Arcturus, http://www.arctur.com/lab_portal/products/pixcell_fluorescence.htm, 2 pages, visited Sep. 21, 2004.

"PixCell® IIe Laser Capture Microdissection (LCM) Instrument—Isolate Cells of Interest Quickly and Conveniently," Arcturus, http://www.arctur.com/lab_portal/products/pixcell_isolate_cells_quickly.htm, 1 page, visited Sep. 21, 2004.

"Preparation Of Paraffin-Embedded Sections For Immunohistochemistry," Chemicon International, http://www.chemicon.com/TechSupp/Protocol/ParaffinProtocol.asp, 3 pages, visited Oct. 21, 2002.

Robinson et al., "Germ cell specific expression of c-kit in the human fetal gonad," *Molecular Human Reproduction* 7(9):845-852, 2001.

"Signal Amplification—Tyramide Signal Amplification," BioProbes 37, p. 17, May 21, 2001.

"The Ciphergenl SELDI Process," Ciphergen Biosystems, Inc., http://www.ciphergen.com/tech_doc11.1.html, 1 pages, visited Aug. 16, 2002.

Tullis et al., "Activities of key metabolic enzymes in the heater organs of scombroid fishes," PubMed (cited from. *Exp Biol* Nov. 1991;161:383-403), 2 pages, visited Nov. 20, 2002.

Office Action dated Apr. 1, 2008 from U.S. Appl. No. 10/543,218.

Englert et al., "Molecular profiling of human cancer: New opportunities," *Current Opinion in Molecular Therapeutics* 1(5):712-719, 1999.

Bénédicte Baisse et al., "Microdissection by Exclusion and DNA Extraction for Multiple PCR Analyses from Archival Tissue Sections," *BioTechniques* 28(5):853-856, 2000.

Bohm et al., "Microbeam MOMeNT: non-contact laser microdissection of membrane-mounted native tissue," *The American Journal of Pathology* 151(1):63-67, 1997 (Abstract).

Burton et al., "Comparison of Histologic Stains for Use in PCR Analysis of Microdissected, Paraffin-Embedded Tissues," *BioTechniques* 24(1):86-92, 1998.

Casciola-Rosen et al., "Lumenal Labeling of Rat Hepatocyte Early Endosomes," *The Journal of Biological Chemistry* 267(12):8213-8221, 1992.

David et al., "Protein Iodination with Solid State Lactoperoxidase," *Biochemistry* 13(5):1014-1021, 1974.

Faulkner et al., "Universal Amplification of DNA Isolated from Small Regions of Paraffin-Embedded, Formalin-Fixed Tissue," *BioTechniques* 24(1):47-50, 1998.

Fend et al., "Composite Low Grade B-Cell Lymphomas with Two Immunophenotypically Distinct Cell Populations Are True Biclonal Lymphomas," *American Journal of Pathology* 154(6):1857-1866, 1999.

Gillespie et al., "The Role of Tissue Microdissection in Cancer Research," *The Cancer Journal* 7(1):32-39, 2001.

Goto et al., "Insulation-like growth factor I is a growth-promoting factor for *Leishmania* promastigotes and amastigotes," *Proc. Natl. Acad. Sci. USA* 95:13211-13216, 1998.

Gygi et al., "Quantitative analysis of complex protein mixtures using isotope-coded affinity tags," *Nature Biotechnology* 17:994-999, 1999.

Han et al., "Quantitative profiling of differentiation-induced microsomal proteins using isotope-coded affinity tages and mass spectrometry," *Nature Biotechnology* 19:946-951, 2001.

Harlow et al., "Cell Staining," *Antibodies A Laboratory Manual*, pp. 359-401, Cold Spring Harbor Laboratory, 1988.

Hiller et al., "Microdissection RT-PCR Analysis of Gene Expression in Pathologically Defined Frozen Tissue Sections," *BioTechniques* 21(1):38-44, 1996.

Janeway et al., "ImmunoBiology The Immune System in Health and Disease," pp. 50-51, Fourth Edition, Current Biology Publications, Garland Publishing, Taylor & Francis Group, New York, New York, 1999.

Lal et al., "Selective Elimination of Lymphocyte Subpopulations by Monoclonal Antibody-Enzyme Conjugates," *Journal of Immunological Methods* 79:307-318, 1985.

Ohyama et al., "Laser Capture Microdissection-Generated Target Sample for High-Density Olignoucleotide Array Hybridization," *BioTechniques* 29(3):530-536, 2000.

Serth et al., "Technical Advance, Quantitation of DNA Extracted after Micropreparation of Cells from Frozen and Formalin-Fixed Tissue Sections," *American Journal of Pathology* 156(4):1189-1196, 2000.

Spect et al., "Quantitative Gene Expression Analysis in Microdissected Archival Formalin-Fixed and Paraffin-Embedded Tumor Tissue," *The American Journal of Pathology* 158(2):419-429, 2001.

Suarez-Quian et al., "Laser Capture Microdissection of Single Cells from Complex Tissues," *BioTechniques* 26(2):328-335, 1999.

To et al., "Technical Advance, Analysis of mRNA from Microdissected Frozen Tissue Sections without RNA Isolation," *American Journal of Pathology* 153(1):47-51, 1998.

von Eggeling et al., "Tissue-Specific Microdissection Coupled with ProteinChip® Array Technologies: Applications in Cancer Research," *BioTechniques* 29(5):1066-1070, 2000.

Watts et al., "In situ $^{125}$I-labelling of endosome proteins with lactoperoxidase conjugates," *The EMBO Journal* 3(9)1965-1970, 1984.

International Search Report from International Application No. PCT/US03/12734.

Office Action dated Apr. 16, 2007 form U.S. Appl. No. 10/511,511.

Office Action dated Apr. 14, 2009 from U.S. Appl. No. 10/543,218.

TARGET ACTIVATED MICROTRANSFER

CROSS REFERENCE TO RELATED APPLICATION

This application is a continuation-in-part of U.S. application Ser. No. 10/543,218, filed Jul. 22, 2005, which is the National Stage of International Application No. PCT/US2003/023317, filed Jul. 23, 2003, which in turn claims the benefit of U.S. Provisional Application No. 60/442,399, filed Jan. 24, 2003, all of which are incorporated herein by reference in their entireties.

FIELD

The present disclosure is related to methods of analysis of biomolecules, particularly methods that involve targeting components of biological samples for subsequent separation of components of interest from their surroundings.

BACKGROUND

A variety of techniques have been used to microdissect specific cells or cell populations from a histological sample under direct microscopic visualization. Original microdissection techniques involved painstaking (and sometimes clumsy) manual dissection using needles or other micromanipulation devices to isolate individual cells based on visible, histological characteristics.

More recent techniques have been developed to more efficiently separate biological components, such as particular subsets of cells, from a whole tissue sample. For example, Emmert-Buck et al. described the use of laser-based microdissection techniques to rapidly procure microscopic, histopathologically defined cell populations. Examples of such laser capture microdissection (LCM) are shown in U.S. Pat. Nos. 5,843,657; 5,843,644; 5,859,699; 5,598,085, and 6,010,888, as well as WO 97/13838; WO 98/35216; WO 00/06992; and WO 00/49410. The disclosure of columns 4-18 of U.S. Pat. No. 6,010,888 is incorporated herein by reference. In LCM, a tissue section is contacted with a transfer member that is selectively and/or focally activated by an external force to adhere target cells to the activated region of the transfer member. For example, a laser beam can be directed in a microscopic field of view toward a portion of the transfer member that overlies the target cells. The laser beam focally activates the transfer member to adhere the target cells to it, and the transfer member is then pulled away from the tissue section to remove the adherent targeted cells from the tissue section for subsequent analysis.

Other microdissection techniques are disclosed in U.S. Pat. No. 6,194,157, which describes overlaying a photoresist (such as those used in etching computer chips) onto a thin tissue section, then activating specific regions of the photoresist using electromagnetic radiation (such as a beam of a laser). Depending on the photoresist used, the "desired" cells are either washed off in the activated areas, or the undesired cells are washed away while the activated photoresist holds the desired cells to the slide. These methods share the same inherent disadvantages of LCM, in that individual cells must be visually identified and targeted before harvest.

A more recent approach to the analysis of biological material is layered expression scanning (LES), as disclosed in WO 01/07915. A biological sample (such as a tissue section) is placed on a layered substrate, in which different layers contain different identification molecules, for example different monoclonal antibodies or nucleic acid probes. Components of the biological sample are then transferred through the layers, by diffusion or electrophoresis, such that different components of the specimen are specifically bound in different layers. The pattern of binding in the different layers can be correlated with the architecture of the biological specimen, to determine different patterns of molecular expression in different regions of the specimen. For example, differences in protein expression can be compared between regions of malignant and non-malignant cells in a heterogeneous tumor specimen.

Another recent advance in the field of microdissection is the transfer microdissection technique shown in WO 02/10751. The transfer of targeted specimen components is accomplished by selectively focally altering a characteristic of a transfer layer adjacent the target region, such that biomolecules can move through the altered area of the transfer layer. In particular examples, the transfer layer is altered by focally increasing a permeability of the transfer layer, for example by selecting and removing a focal portion of the transfer layer. The biomolecules are then transported through the altered region of the transfer layer, to microdissect the biomolecules of interest from the biological sample. Transfer microdissection allows biomolecules from regions of interest in the biological specimen (such as nests of highly atypical cells in a tumor section) to be selectively analyzed.

Although these microdissection techniques have provided powerful tools for the selective analysis of biological specimens, and are a substantial improvement over prior techniques, they are still not highly susceptible to automation for high-throughput analysis of multiple specimens. These techniques still rely on selection of a targeted structure, for example by microscopic visualization and manual targeting with a laser beam that is directed at the target to adhere it to an overlying thermoplastic film.

SUMMARY

The present disclosure describes methods, systems and devices for analyzing a biological sample, such as a cellular specimen. In one aspect of the method, a proximal activating event comes from within the biological sample for focally altering an adjacent transfer surface for selective removal of a target from within the sample. In situ activation from within the sample avoids the necessity of selecting each target and then altering the transfer surface by application of external energy, as in laser capture microdissection. The method of in situ or target activated alteration allows for more automatic identification and removal of the target, allows individual scattered cells to be collected for molecular profiling, and improves collection of cells when histological identification of targets is challenging or impossible. The self-identification and selective adherence of the targets to the transfer surface permits a significant increase in the efficiency of transfer microdissection, and enables high-though-put methods of analysis.

Another aspect of the disclosure is a method of removing a target from a biological sample by contacting the biological sample with a reagent that selectively acts on the target within the biological sample. A transfer surface (such as a thermoplastic film) is placed adjacent the biological sample, and the reagent produces a change that selectively affects the transfer surface. For example, this change focally adheres the target to the transfer surface such that the target can be selectively removed from the biological sample by removing the transfer surface and the adhered target from the biological sample. Alternatively, the reagent focally increases the permeability of the transfer surface to the target, such that the target can move through the area of increased permeability in the transfer surface.

Also disclosed herein are kits and devices for performing target activated transfer. In particular examples the kit contains the transfer surface and reagent. The device contains a mounting surface that is irradiated by the light source which triggers target activated transfer.

In a further embodiment, there is disclosed a device for performing target activated transfer from a tissue sample in which a localized reagent specifically determines the microadhering of desired cellular material in the tissue sample. The device includes a mounting surface for mounting a tissue sample; and a light source positioned to substantially uniformly irradiate both stained and unstained regions of the tissue sample with light energy that activates the reagent to selectively adhere the stained regions to a transfer surface.

Also described herein is an automated system for transferring tissue from a tissue sample to a transfer substrate. The system includes means for holding a tissue section that includes targets specifically stained with an absorptive stain thereby resulting in a stained tissue surface, and a flexible transfer film that includes a lower thermoplastic layer in sufficient thermal contact with the stained tissue surface; an irradiating assembly configured to provide a predetermined uniform light dose to the entire tissue section; and means for applying a constant pressure to the transfer film during irradiation.

In another example, there is disclosed an automated system that includes a tissue transfer station that includes an irradiating assembly, an x-y translating stage configured to translate a tissue slide upon which a tissue section can be mounted, and means for generating an air-bearing between the irradiating assembly and a transfer substrate that is positioned over the tissue sample; and a controller for controlling the position of the x-y translating stage.

According to a further embodiment, described herein is a method of automatically isolating light-absorptive targets from a sample surface that involves placing a flexible transfer film in contact with the sample surface that includes stained surface regions; simultaneously irradiating the sample surface and applying a substantially constant pressure on the transfer film to maintain thermal contact between the transfer film and the sample surface during transient heating of the stained surface regions to selectively adhere the absorptive targets to the transfer film; and selectively transferring the adhered absorptive targets to the transfer film as the transfer film is removed from the sample surface.

The features and advantages of the disclosed methods and devices will become more apparent from the following detailed description of several embodiments, which proceeds with reference to the accompanying figures.

BRIEF DESCRIPTION OF THE DRAWINGS

FIG. 6A illustrates an embodiment in which targeting and activating moieties of the reagent are directly attached to one another. FIG. 6B illustrates an embodiment in which the targeting and activating moieties are both linked to a polymer substrate. FIG. 6C shows the targeting and activating moieties attached to the polymer substrate by linkers, while FIG. 6D illustrates multiple targeting moieties and activating moieties each attached to the polymer substrate by a linker.

FIG. 9C is an image of the transfer film after microdissection, and in FIG. 9D arrows point to basal cells that remain after microdissection.

DETAILED DESCRIPTION

I. Abbreviations

Figure 1A:
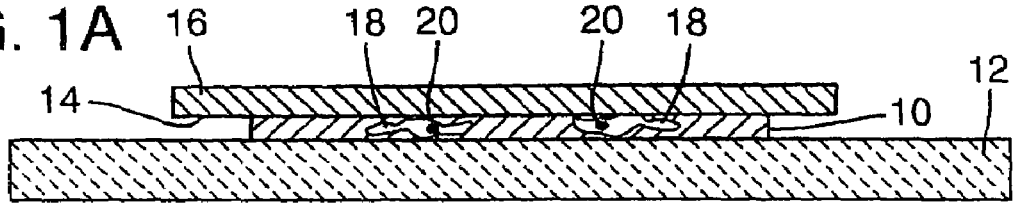
FIGS. 1A, 1B and 1C are a series of cross sectional schematic enlarged views illustrating one embodiment of target activated transfer, in which a reagent in the target region of a tissue section focally activates adhesion of the target to a transfer surface.

DCTM: direct cell target microtransfer
DNA: deoxyribonucleic acid
ELISA: enzyme-linked immunosorbant assay
IgG: immunoglobulin G
IR: infrared
LCM: laser capture microdissection
OD: optical density
PBS: phosphate buffered saline
PCR: polymerase chain reaction
RNA: ribonucleic acid
SATA-SMCC
SELDI: surface enhanced laser desorption and ionization
TAT: target activated transfer

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided. In case of any conflict between the meaning of terms used herein and in an incorporated document, the terms in this specification control.

Activating moiety: A moiety that participates in altering a transfer surface. The activating moiety can act directly on the transfer surface, for example by releasing heat to partially melt the surface. Alternatively, the activating moiety can act in association with another activating agent, such as light that is absorbed by the activating moiety and emitted as heat. In other examples, the activating moiety acts in association with intermediary agents, such as a substrate for a catalytic activating moiety.

Adherence: A physical association of two surfaces held together by interfacial forces. An example of adherence is the force provided by an adhesive, such as a thermoplastic material that melts to physically attach to another object.

Amplification: Techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification may be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Antibody: Immunoglobulin molecules and immunologically active portions of immunoglobulin molecules, i.e., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains inter-connected by disulfide bonds. However, it has been shown that the antigen-binding function of an antibody can be performed by fragments of a naturally occurring antibody. Antibody fragments that perform the antigen-binding function of an antibody are within the scope of the disclosure.

Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faoulkner et al., *Nature* 298:286, 1982; Morrison, *J. Immunol.* 123:793, 1979; Morrison et al., *Ann Rev. Immunol* 2:239, 1984).

Antibody-enzyme fusion: A chimeric fusion molecule that includes an antibody, or the variable binding domain of an antibody fused to an enzyme moiety.

Binding partner: Any molecule or compound capable of recognizing and binding to a specific structural aspect of a corresponding molecule or compound. Examples of such binding partners and corresponding molecule or compound include: antigen/antibody, hapten/antibody, nucleic acid probe/complementary nucleic acid sequence, lectin/carbohydrate, apoprotein/cofactor and biotin/(strept)avidin.

Direct Cell Target Microtransfer (DCTM) molecule: A molecule having at least two functional moieties: a targeting moiety (also called a localizing moiety, because it localizes the DCTM molecule to a target cell or site within a sample), that targets specific components (such as cells or structures within or upon those cells); and an activating moiety, that facilitates the adherence of the transfer substrate to the targeted components. In specific embodiments, these two moieties are attached directly to each other. In others, they are attached through a linker. DCTM molecules are more fully described in PCT/US03/12734, which disclosure is incorporated by reference.

Electromagnetic radiation, and activation of reagent: Electromagnetic radiation is a form of energy in which an oscillatory electric field and an oscillatory magnetic field are perpendicular to one another, and to the direction of propagation of the direction of propagation of the radiation. Light is the name often given to the visible spectrum of electromagnetic radiation. All of these forms of radiation transfer energy, and are capable of activating light responsive reagents, such as chromophores and heat-generating catalysts.

Fusion protein: Proteins that have at least two domains or moieties fused together, each portion of the protein comprising a region capable of independent structural or functional activity (for instance forming a specific complex with a target molecule, or carrying out a biochemical reaction). In some embodiments, the two domains are either genetically fused together (for example nucleic acid molecules that encode each protein domain are functionally linked together) or chemically fused together (for example covalently bonded). By way of example, a linker oligonucleotide may be produced such that it encodes both the targeting and activating moieties within a single polynucleotide molecule. The translated product of such a fusion-encoding polynucleotide is the fusion protein. In other embodiments, chemical linkers may be used to join targeting and activating moieties to form fusion proteins.

Immunocytochemistry: The identification of antigens in a biological sample (for example tissue section, smears, cell culture) using specific immunological (antibody-antigen) interactions culminating in the attachment of a visible marker to the antigen. Examples of visual markers used in immunocytochemistry are fluorescent dyes, colloidal metals, haptens, radioactive markers, and enzymes that convert an externally supplied substrate into a visible indicator molecule, such as an absorbing, fluorescent or luminescent molecule. Immunocytochemistry techniques are known to those of skill in the art, and examples of such techniques are those included in Ausubel et al. (In *Current Protocols in Molecular Biology*, Greene Publ. Assoc. and Wiley-Intersciences, 1998).

Isolated: An "isolated" biological component (such as a cell, cell type, nucleic acid molecule, protein or organelle) has been substantially separated or purified away from other biological components in the environment in which the component naturally occurs, i.e., other chromosomal and extra-chromosomal DNA and RNA, proteins and organelles. By way of example, a component can be isolated from a cell or a biochemical reaction mixture, or specific cells can be isolated from a complex tissue.

Linker: A linker is a "chemical arm" between two moieties or domains in a molecule. Linkers may be used to join otherwise separate molecular moieties. The term "linker" also refers to the part of a molecule between two moieties.

Microtransfer: A process of isolating an element from a sample, often a tissue sample, at a microscopic level through facilitating adherence of that element to a transfer substrate, or selectively allowing migration of the element through a focal region on the substrate, to physically separate the element from the remaining components. In some examples, the microtransfer is used to separate cells or cellular components from a sample based upon a distinguishing characteristic (such as expression of a cell antigen or receptor) or pattern of expression (such as expression of a protein, nucleic acid, or other molecule that is the target of the targeting moiety) within the sample.

Moiety: A part or portion of a molecule having a characteristic chemical, biochemical, structural and/or pharmacological property or function. As used herein, the term moiety refers to a subpart of a molecule that retains an independent biochemical or structural activity from the remainder of the molecule, for instance the ability to generate heat or fluoresce, or to bind or associate with a target or to carry out an enzymatic reaction. A single molecule may have multiple moieties, for instance an antigen-binding moiety and a fluorescing moiety, each having a different function.

Operably linked: A first molecule (e.g., nucleic acid sequence, protein, linker, etc.) is operably linked with a second molecule when the first molecule is placed in a functional relationship with the second molecule. For instance, a promoter is operably linked to a coding sequence if the promoter affects the transcription or expression of the coding sequence. Generally, operably linked DNA sequences are contiguous and, where necessary to join two protein-coding regions, in the same reading frame.

Polymer: Polymers are substances (e.g., protein, nucleic acid sequences, transfer substrates) consisting of large molecules that are made of many small, repeating units called monomers. The number of repeating units in one large molecule is called the degree of polymerization.

The class of polymers includes thermoplastic or electroactive polymers. Examples of thermoplastic or electroactive polymers that may be used in conjunction with the methods disclosed herein include ethylene-vinyl acetate copolymer (EVAc), polyethylene (PE), and polyaniline (PANi) films (see Kamalesh et al., *J. Biomed. Mater. Res.* 52(3): 467-478, 2000) and those set forth in U.S. Pat. No. 6,242,503 to Kozma et al., which also describes methods of making such polymers.

Particular thermoplastic polymers may be applied in a powder or liquid form, and caused to form adhesive films (e.g., by melting the powder and resolidifying the liquid polymer on cooling). Examples of commercial-grade thermoplastic polymers include DuPont ELVAX 510 and ethylene-vinyl acetate copolymer.

Probes: An isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are known, e.g., Sambrook et al. (In *Molecular Cloning: A Laboratory Manual*, CSHL, New York, 1989) and Ausubel et al. (In *Current Protocols in Molecular Biology*, John Wiley & Sons, New York, 1998).

Reagent: Any substance used for the purpose of detecting, measuring, examining, or analyzing other substances. This term includes both organic and inorganic reagents. An immunoreagent is a reagent that includes an antibody or antibody fragment for targeting the reagent to a target.

Separate(d)/Separation: To spatially dissociate components, such as biomolecules, cells, or cell clusters, from their surrounding natural environment, for instance by physically removing the components (for example by causing adherence of selected components to a transfer substrate). Separation may be employed to isolate selected components for subsequent analysis of the characteristics of the separated components.

Separation can be effected on various scales, for instance large-scale physical dissection wherein the operator visualizes the process, and small-scale microtransfer or microdissection wherein the operator uses a visual aid (such as a microscope) to accomplish the separation.

Separation is not an absolute term (in that separation need not be perfect or "complete" for components to be "separated").

Specific binding agent: An agent that binds substantially only to a defined target. Thus a protein-specific binding agent binds substantially only to the defined protein, or a peptide region within a protein. As used herein, the term "specific binding agent," refers to a specific protein or peptide, including antibodies (and functional fragments thereof) and other agents (such as soluble receptors or ligands for receptors) that bind substantially only to target proteins or nucleic acids. In some embodiments, these target proteins or nucleic acids are within target cells of interest.

Antibodies may be produced using standard procedures described in a number of texts, including Harlow and Lane (*Antibodies, A Laboratory Manual*, CSHL, New York, 1988). The determination that a particular agent binds substantially only within the target cells may readily be made by using or adapting routine procedures. One suitable in vitro assay makes use of the Western blotting procedure (described in many standard texts, including Harlow and Lane, *Antibodies, A Laboratory Manual*, CSHL, New York, 1988). Western blotting may be used to determine that a given protein binding agent binds substantially only to the specified protein.

Shorter fragments of antibodies can also serve as specific binding agents. For instance, FAbs, Fvs, and single-chain Fvs (SCFvs) that bind to a protein or peptide within a target cells would be target cell-specific binding agents. These antibody fragments are defined as follows: (1) FAb, the fragment that contains a monovalent antigen-binding fragment of an antibody molecule produced by digestion of whole antibody with the enzyme papain to yield an intact light chain and a portion of one heavy chain; (2) FAb', the fragment of an antibody molecule obtained by treating whole antibody with pepsin, followed by reduction, to yield an intact light chain and a portion of the heavy chain; two FAb' fragments are obtained per antibody molecule; (3) $(FAb')_2$, the fragment of the antibody obtained by treating whole antibody with the enzyme pepsin without subsequent reduction; (4) F(Ab')2, a dimer of two FAb' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Target: A sub-portion of a biological sample that is desired to be removed from the biological sample. The sub-portion can include a cell, cellular component, or a biomolecule (such as a protein or nucleic acid). Particular non-limiting examples are a portion of a histological specimen (such as a nest of malignant cells within the epithelium of a tissue section of a prostate); a particular type of cell (such as a leukocyte, or even a CD4+ cell); a cell that expresses a particular protein (such as a tumor promoter protein); a cell that carries a particular receptor on its surface (such as an estrogen receptor); a particular molecule (such as an m-RNA molecule associated with the expression of a biomolecule of interest), or a portion of the biological sample that has a common chemical characteristic (such as the property of being stained by a specific histological stain such as eosin). The target is sometimes (although not always) spread throughout the biological specimen, but is characterized by a common physiochemical or biological property (such as recognition by a specific binding agent) that allows the target to be specifically recognized in the biological sample.

The target may also include non-specific material, and need not be purely a cell, cellular component or biomolecule of interest. For example, the target may include some incidental adherent material that is removed with a cell or biomolecule of interest.

Target Activated Transfer: Removal of a target from a biological sample by alteration of a transfer substrate, wherein the target alters the transfer substrate to help effect the removal.

Targeting Moiety: A moiety that selectively binds to or otherwise localizes in or adjacent a target. Non-limiting examples include an antibody, receptor, ligand or probe.

Thermoplastic: A material that softens when exposed to heat and returns to it original condition when cooled to room temperature. For example, ethylene vinyl acetate copolymer resins form a family of thermoplastics that (depending on molecular weight and chemical composition) can be extrudable, foamable, injection moldable, blow moldable and suitable for compounding with other olefinic resins and rubbers to form hot glues. Specific formulations of EVA's can be extruded into strong, thin, transparent transfer films which can then be focally activated to effect a thermoplastic adhesive bond to specific targets.

Trigger event: "Trigger event" refers to an event that affects the reagent, such that the reagent alters the transfer surface. In a non-limiting example, the trigger event changes the reagent, which in turn changes the transfer surface. This change in the transfer surface permits selective removal of the target from the biological sample. In yet another example, the trigger event changes the target, which makes the target susceptible to selection (for example by selective heating of the target).

Transfer substrate and surface: A transfer substrate is a material (such as a thermoplastic polymer) that serves as a substrate for selective adhesion or transmission of the target, for selective removal of the target from the biological sample. A transfer surface is a transfer substrate provided on a layer, and the transfer substrate may alternatively be referred to as a transfer layer.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising" means "including." Similarly, the word "or" is intended to include "and" unless the context clearly indicates otherwise. Hence "comprising A or B" means "including A, B, or A and B." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict between an incorporated document and this specification, the present specification, including explanations of terms, will control. In addition, the materials, methods, and examples are illustrative only and not intended to be limiting.

III Description of Several Specific Embodiments

Disclosed herein are methods and devices for removing a target (such as a subset of cells) from a biological sample (such as a tissue section or cellular preparation) by using an in situ activating event from within the biological sample to alter a transfer surface for subsequent removal of the target from the sample. In some particular examples, the activating event focally adheres the target to a transfer surface that is in contact with the sample. Alternatively, the activating event focally increases the permeability of the transfer surface to the target, so that the target can selectively pass through the overlying/adjacent transfer surface.

The activating event that alters the transfer surface can be provided by a reagent that specifically binds to the target and performs the activating event that alters the transfer surface. In one example, the reagent includes a chromophore that can be stimulated with light to emit heat. After the biological specimen is exposed to the reagent to selectively bind it to the target and concentrate the reagent within the target, a transfer surface (such as a thermoplastic film) is placed in contact with the biological sample. Exposing the biological sample to light stimulates the chromophore to produce a change in or adjacent the target that selectively affects the transfer surface.

Heat emitted from the chromophore focally heats the transfer surface to selectively adhere the target to the transfer surface, such that removal of the transfer surface from the biological sample also selectively removes the target from the sample. "Selective removal" does not imply that only the target is removed from the sample, but rather that target is removed from a larger biological sample that contains more than the target. In some instances the selectively removed target will include biological material other than that specifically desired, but the level of non-desired material will have been substantially reduced from that seen in the original biological sample.

In most instances, multiple targets that share a similar characteristic will be present within the biological sample, and many of these targets will specifically bind the reagent and focally alter the transfer surface, such that the multiple targets within the sample can be efficiently and quickly removed, with a minimum of selection by an operator. This feature of target "self-selection" based on physical, chemical or biological characteristics of the target allows efficient removal of the target.

The target activated transfer method differs from standard laser capture microdissection in that the transfer surface is altered from within the biological sample, instead of being changed from outside the sample by application of external laser energy to the transfer surface. Providing an internal (sample based) event, instead of an external force, to alter the transfer surface provides an accurate focal alteration of the transfer surface. Molecular targeting of the reagent to individual scattered cells (for example using an antibody or probe) allows target cells to be collected, even when histological identification of the cells is challenging or impossible. Moreover, by targeting the reagent to specific molecules or structures of interest within the sample, this method is readily suitable to automation. Furthermore, due to the specificity of the method for target cells or cell components of interest, this method reduces the number of cells needed to obtain molecular profiling information in comparison to existing molecular profiling systems, and decreases the need for amplification of molecules due to decreasing amplification bias.

Replacing the "human dissector" with an "antibody/probe dissector" permits the technique to become operator-independent. This change allows certain embodiments of the method to become several orders of magnitude faster than traditional laser capture microdissection (LCM), in which the investigator needs to tediously dissect each cell/gland one at a time. It often requires 10,000-100,000 individually-executed laser shots for each histology slide used in a study, thus a standard LCM dissection may require several hours to procure the cells from each slide, and days/weeks to complete an entire study. In contrast, target activated transfer method disclosed herein can often procure substantially all of the targeted cells in each slide in just a few seconds using a single wide-field laser pulse.

In a simplified schematic example shown in FIG. 1A, a tissue section 10 has a bottom surface adhered to a glass support slide 12 with polylysine. A top surface of tissue section 10 is in contact with an overlying transfer surface 14 of a planar transfer member 16, which in this example is a thin film with a thermoplastic surface. Tissue section 10 contains cellular structures 18 (such as prostate epithelial tissue) that include a target 20 (such as an area of highly atypical cells). The thermoplastic film is capable of being focally melted in locations where the surface contacts the targets and reagent. In this example, transfer member 16 is placed on top of and in contact with tissue section 10, such that transfer surface 14 is in substantially contiguous contact with the biological specimen. Such contiguous contact can be achieved, for example, by pressing transfer member 16 against tissue section 10. The biological specimen contains the reagent (not shown), which localizes in targets 20 and focally heats thermoplastic surface 14 of member 16. Localization of the reagent in the targets is achieved, for example, with a specific binding agent that specifically binds the reagent to the target.

Figure 1B:
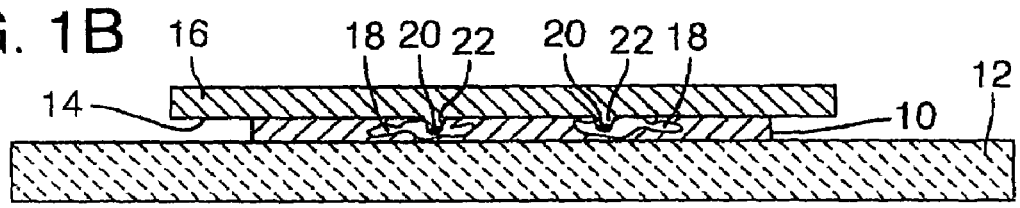
Figure 1C:
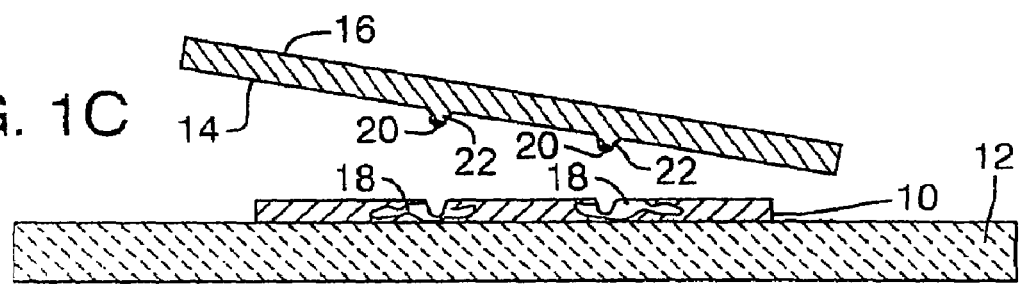

FIG. 1B schematically illustrates changes that occur in transfer member 16 after the reagent heats the adjacent surface of the transfer member to adhere it to the targets. As the thermoplastic surface 14 adjacent the targets heats and melts, the thermoplastic material focally flows down and perhaps around targets 20 to form a physical connection 22 that adheres the targets to transfer member 16. As shown in FIG. 1C, transfer member 16 is then lifted away from tissue section 10, which selectively removes targets 20 from the tissue section, while substantially leaving non-targeted material in tissue section 10. The precision of removal of each target can vary depending on a variety of circumstances, such as the size and shape of the target, and the histological architecture of surrounding tissue. Moreover, the specificity of removal of only target tissue from surrounding tissue need not be 100%, but can vary depending on the end use to which the target tissue is to be put. It is sufficient, in many embodiments, if the specificity of removal of target tissue is small (for example the desired target is only 5% or less of the removed material). However, the flexibility and precision of this method can also permit specificity of removal of at least 10%, 30%, 50%, 75%, 90%, 95% or more (that is, at least that percentage of the removed tissue is the desired target). Variation of parameters that affect the precision of target capture are known to those of skill in the art, and include varying the thickness of the tissue section or other characteristics of the biological sample.

Figure 2:
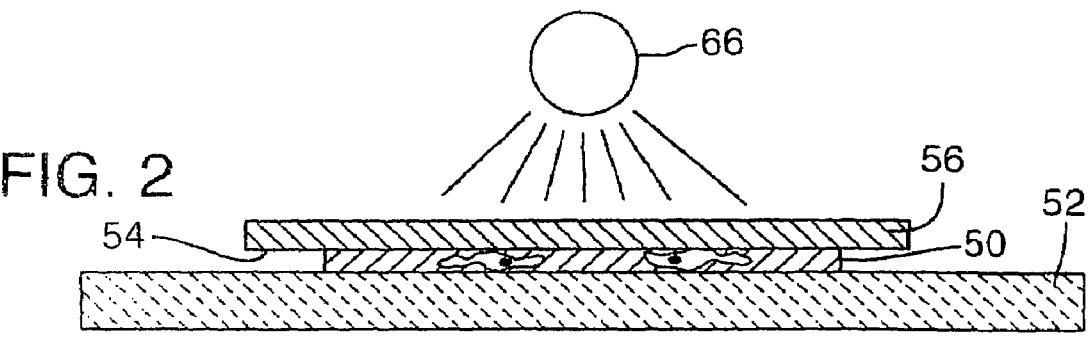
FIG. 2 illustrates an embodiment of the method shown in FIG. 1, wherein the reagent in the target is activated by electromagnetic radiation, such as diffuse light from a flash lamp, which briefly illuminates a large region of the slide including both specific targets and unwanted (unlabelled) cells.

A particular advantage of some embodiments of this technology is that the reagent can be activated by an external stimulus or trigger event, even though the proximate event that alters the transfer surface comes from within the biological sample. FIG. 2 illustrates an embodiment in which the reagent is activatable by electromagnetic energy, such as light energy. For example, the reagent is an immunostain that carries an absorbing dye (such as a chromophore) that emits heat when exposed to light of a specified activating wavelength or wavelengths. In particular examples, the activating wavelength is for example about 815 nanometers.

Figure 3:
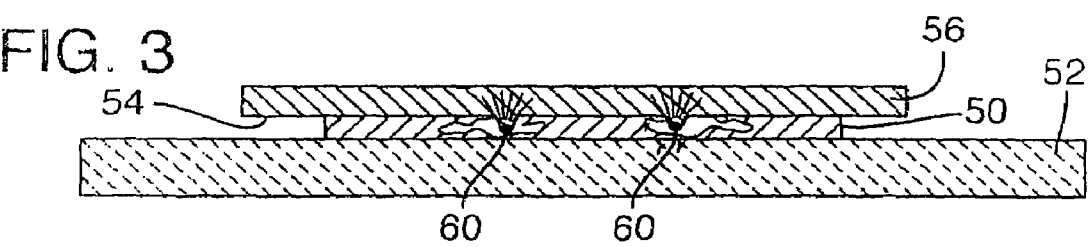
FIG. 3 illustrates an embodiment of the method shown in FIG. 1, wherein the reagent in the target emits heat to melt overlying regions of the transfer surface, to fuse the target to the transfer surface.

FIG. 2 illustrates an embodiment in which a tissue section 50 is mounted on a support slide 52, and covered by a thermoplastic film 56 having a transfer surface 54. A light source 66 is provided in a position (such as above transfer film 56) that non-specifically illuminates the entire surface of tissue section 50, to supply energy to the chromophore that is concentrated at the targets. The electromagnetic energy supplied by the light is then converted into heat by the reagent, as shown in FIG. 3, to fuse targets 60 to transfer surface 54. Preferably, thermoplastic film 56 is transparent and absorbs little if any of the incident light, to minimize non-specific adherence of tissue section 50 to transfer film 56.

In other embodiments, the reagent does not carry an absorbing dye, but instead selectively deposits a contrast material (such as a dark precipitate) at the targets. This dark precipitate selectively absorbs more light than surrounding non-pigmented tissue, such that thermoplastic surface 54 is focally melted to fuse the transfer surface to the targets. Alternatively, the reagent includes a photo-activated material (such as a liposome that is disrupted by exposure to light of the type shown in U.S. Pat. Nos. 4,882,165; 5,257,970; or 5,277,913). The light stimulated disruption of the liposome can release heat-generating chemicals after the reagent has been delivered to the target The tissue specific stain (chromophore) can include additional components to provide for greater efficiency or ease of bonding. For example it can also include a liposome containing a photo-activatable molecule. In such cases the light absorbed by the chromophore heats and disrupts the liposome focally so that a subsequent photoactivating flash (e.g., at a different shorter wavelength specific to the photo-polymerization of the adhesive) causes target bonding to the transfer film selectively only where the liposomes were disrupted. The non-disrupted liposomes contain internally photopolymerized molecules not able to make bonds to overlying transfer films.

Alternatively, the substrate on which the tissue is placed or the transfer film surface includes a photo-activated material (such as a photoresist or photopolymerizable adhesive). In this case the activating light is transmitted through the tissue layer first and then the photoresist/photopolymerizable layer, and a negative pattern of adhesion is created relative to the target specific chromophore staining (i.e., the stained regions protect the underlying photoactivatable layer). It this case the bonding to the substrate or transfer film would include all cells not specifically stained with the chromophore thereby leaving the desired sample on the complementary surface.

In yet other embodiments, the reagent does not require activation, or it undergoes activation by something other than electromagnetic energy. For example, the reagent is an immunoreagent that includes an enzyme such as horseradish peroxidase that is activated by exposing the biological sample to diamino benzene (DAB); alkaline phosphatase that is activated by 2-5'-chloro-2-phosphoryloxyphenyl)-6-chloro-4 (3H)-quinazolinone, NABP/new fuchsin, or NBT/BCIP; or beta-galactosidase that is activated by exposure to BCIG. Activation of the enzyme in this example deposits a precipitate that gives the target a sufficiently greater optical density than the surrounding tissue, thereby allowing the target to absorb more incident light or other electromagnetic radiation, and focally melt the overlying thermoplastic layer to fuse the target to it.

In yet another example, the reagent specifically binds to the targets, and carries a heat-generating enzyme that does not require external activation. Hence the targets will heat once the biological material is exposed to the reagent, and the targets will automatically self-identify themselves and fuse themselves to the thermoplastic material.

Figure 4A:
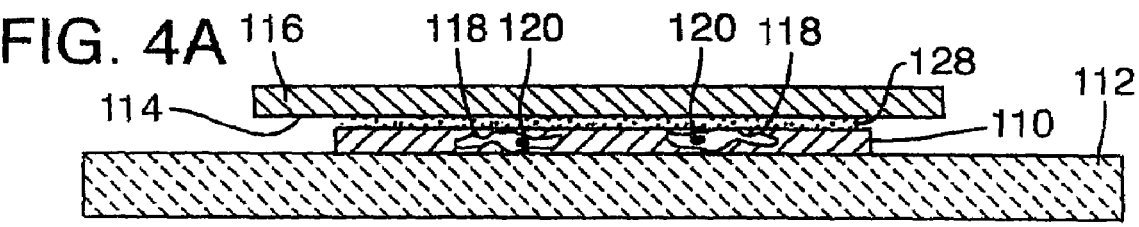
FIG. 4A illustrates an embodiment of the method in which a layer of thermoplastic particles are placed between the tissue section and transfer surface, to provide a readily meltable substrate for focally fusing the target to the transfer surface.
Figure 4B:
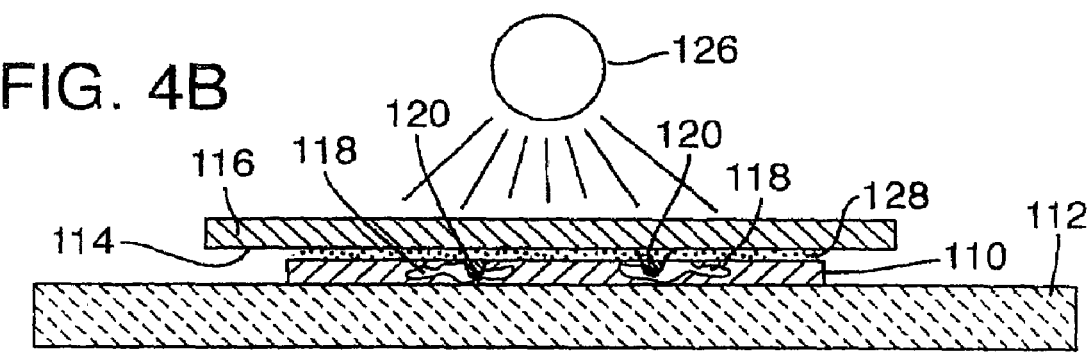
FIG. 4B illustrates light-activation of a reagent in the target region of the tissue section to fuse the melted thermoplastic particles to the target.

In some embodiments, the efficiency of thermal activation (melting) of the thermoplastic material sufficient to create a focal bond to the transfer film can be increased by providing a layer of thermoplastic particles 128 between the tissue section 110 and a transfer layer 116, as shown in FIG. 4A. Upon exposure to an energy source 126 (such as a flash lamp that illuminates tissue section 110 mounted on support 112), targets 120 absorb the energy and generate more heat than surrounding tissue. Energy source 126 can provide a constant source of light, or intermittent light pulses (such as in a flash lamp or laser diode that repeatedly pulses). For conventional immunostained tissues with a large contrast caused by high local optical density of the stain, the light irradiation is on the order of 1 J/cm$^2$ within a time brief enough to avoid major thermal loss to surrounding unstained regions. For example for about 60 μm resolution transfers, the energy is delivered within about 50 msec. A conventional flashlamp that has a pulse length on the order of 1-100 μsec and delivers 10-100 J per pulse is ideal for large area direct transfer activation. Repetitive pulses at near this threshold value provide stronger bonds than a single pulse of the same energy, but also a sharper sensitivity to local stain/chromophore concentration than using a single pulse of greater energy density to heat targets 120. The greater temperature of the targets focally heats the overlying layer of thermoplastic particles to focally melt particles 128 adjacent targets 120 to fuse targets 120 to the inner surface 114 of overlying transfer layer 116. The transfer layer 116 (or its surface) need not be thermoplastic in this embodiment (although it may be), as long as the thermoplastic material of which the particles are made is capable of fusing targets 120 to transfer layer 116. Alternatively, transfer layer 116 can be a material that changes chemical composition in response to melting of particles, for example chemically bonding to the particles or tissue when heated, to thereby adhere target 120 to layer 116.

Low melting temperature thin (~40 μm) thermoplastic polymer (Dupont ELVAX™ 450) films exposed to ~1 J/cm$^2$ create a good thermoplastic bond with tissue sections. Less absorbed energy may be used if the heat generated by chromophore absorption activates a chemical bonding reaction such as a thermally sensitive polymerization. Such chemical polymerization is generally avoided to minimize crosslinking reactions that may alter biological macromolecules of interest in the target, and alter their downstream analysis. However, this problem is minimized by confining the chemical bonding to a thin layer that excludes the tissue section. For example, antibody labeled polystyrene latex microspheres are used to bind to the tissue section surface, and a transfer film is then placed over the bound microspheres to chemically covalently crosslink either specifically with the antibody or the surface of the microspheres (but not to the tissue directly). In this case, the tissue surface is reacted with an immunoreagent to recognize targets, and then the transfer film is applied that rapidly chemically bonds the immunoreagent without any light or additional external energy source. The film surface may also have a layer of chemical reactants suitable for crosslinking.

Figure 5:
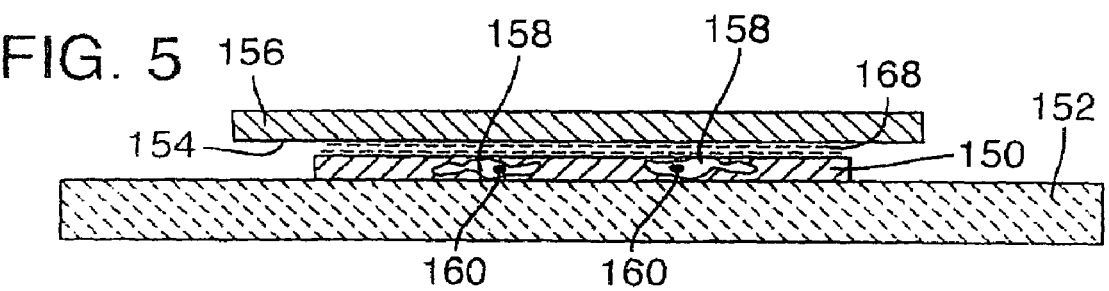
FIG. 5 is a view similar to FIG. 4A, but wherein a liquid or semi-liquid layer of material is placed on the tissue section under the transfer surface prior to activation of the reagent in the target region. Activation of the reagent alters the liquid or semi-liquid layer, for example by inducing focal polymerization or solidification and fusion to the overlying transfer surface.

FIG. 5 shows yet another embodiment of the method, in which tissue section 150 is mounted on support slide 152, and is covered by a transfer member 156 having an inner surface 154. A layer of liquid or semi-solid heat-activated material 168 is applied to the surface of tissue section 150 before transfer member 156 is placed in contact with material 168. The reagent that specifically localizes in targets 160 of tissue section 150 then changes the material 168 to alter the overlying surface 154 of transfer member 156. For example, material 168 may be a heat polymerizable layer that solidifies to bond to the overlying transfer member 156 when heated (where bonding to the transfer member is an "alteration"). Heat emitted by the reagent, which is localized in the targets, focally polymerizes the layer to focally adhere targets 160 to member 156. Transfer layer 156 is then peeled away from material 168 and tissue section 150 to selectively remove targets 160 from the tissue section.

Alternatively, material 168 may be acted upon by the target-localized reagent to focally increase the permeability of transfer member 156 above each target 160, so that transfer microdissection with a layered expression scan can be performed as shown in WO 0210751, which is incorporated by reference. For example, the transfer surface is placed in contact with multiple contiguous porous (e.g. nitrocellulose) layers, and biomolecules from the targets are moved through the regions of increased permeability into and through the nitrocellulose layers by capillary movement or electrophoresis. Each of the layers includes, for example, specific binding molecules (such as antibodies, probes, soluble receptors or ligands) that bind biomolecules of interest from within the targets.

Several schematic examples of the reagent that specifically binds to the target are illustrated in FIGS. 6A-6D. In FIG. 6A, the reagent is shown to include both a targeting moiety to localize the reagent in the target, and an activating moiety to activate the change that adheres the target to the transfer surface, or focally alters the transfer surface so that the target can that selectively move through the transfer surface. The targeting moiety and activating moiety are directly attached to one another in the embodiment of FIG. 6A. For example, the reagent is an immunoreagent in which a specific binding agent (such as an antibody, receptor or probe) is directly attached to a chromophore.

An alternative embodiment of the reagent is shown in FIG. 6B, in which the targeting and activating moieties are each attached to a polymer substrate instead of directly to one another. In FIG. 6C, the targeting and activating moieties are each attached to the polymer substrate by linkers. In FIG. 6D, the multiple targeting and activating moieties are each attached to the polymer substrate by a linker.

In particular examples, the targeting moiety is a nucleic acid molecule capable of specifically binding by hybridizing to a complementary nucleic acid sequence within the target (such as an mRNA sequence that is selectively expressed in malignant cells). Alternatively, the targeting moiety is an antibody that specifically binds to the target, for example an antibody that specifically binds to a cell surface antigen associated with a particular type of tumor, for example the prostate specific antigen (PSA). In another example, the targeting moiety is a ligand that specifically binds to a receptor protein within or upon the target, such as a ligand for an estrogen receptor that is expressed on the surface of certain types of estrogen receptor positive (ER+) breast tumor cells. In certain examples, the targeting moiety may be a secondary targeting moiety that recognizes a primary targeting moiety, as in the case of a secondary antibody that recognizes a primary antibody that is already selectively bound to the target.

The activating moiety may include a catalytic domain that catalyzes a reaction that selectively acts on or adjacent the target, to change the transfer surface adjacent the target. Examples of such a catalyst include an adherence catalyzing enzyme, such as a heat generating enzyme, an enzyme that catalyzes a chemical reaction in the transfer layer, or an enzyme capable of depositing a light absorptive precipitate in the presence of a substrate. In some examples in which the catalyst acts upon a substrate (for example to deposit the light-absorptive precipitate), the method further comprises adding the substrate to the biological specimen to allow it to interact with the catalyst. For example, if the catalytic domain is alkaline phosphatase, peroxidase, or beta-galactosidase, the respective substrates of these catalysts are introduced into the biological specimen to deposit the precipitate after exposing the specimen to the reagent.

The biological sample on which the method is performed can include a broad variety of biological materials, such as a preparation of cells, biopsy material, a tissue section, a cell culture preparation, or a cytology preparation. The sample can either be a coherent tissue specimen with recognizable histological architecture, or a processed or liquid specimen that has been derived from a tissue or other biological specimen, such as a cell suspension or cell culture. In particularly disclosed examples, the biological sample is a standard tissue section, such as a paraffin section that has undergone routine formalin fixation. The specimen may or may not have been stained (for example with eosin) to visualize cellular components of the specimen. Although such staining is often needed in techniques such as laser capture microdissection, which require visualization of stained components of the specimen, such staining is not needed in the present method in which the reagent localizes, self-identifies and adheres itself to the transfer surface.

After the target is selectively removed from the biological sample, it may be subjected to a biological analysis of the target. The target is first exposed to targeting moiety in the form of a primary antibody that selectively binds to the target, and then exposed to a secondary antibody that carries the activating moiety. The activating moiety is then activated (for example by supplying a substrate for an enzymatic activating moiety, or irradiating the slide), adherence to the transfer surface is accomplished, and the transfer surface (with adhered target) is removed from the biological sample and introduced into a container, such as an analysis tube. The analysis (or analyses) carried out can include determining whether biomolecules of interest are present or absent, quantifying a biomolecule in the target, and/or amplifying the target (for example using the polymerase chain reaction). In certain examples, the analysis can include screening for the presence of a protein, or a nucleic acid encoding the protein, wherein the presence or absence of the protein in the target is indicative of a disease in the subject. For example, the test could screen for the presence of an oncogene or an expressed protein associated with malignant tumors (or associated with tumors having particularly good or poor clinical prognoses).

Cells or cell components adhering to the transfer substrate can be procured and analyzed using techniques such as those disclosed in Bonner et al., *Science* 278(5342): 1481-1483, 1997; and Emmert-Buck et al., *Science* 274(8): 998-1001, 1996).

These general principles of the method are further illustrated by the following non-limiting Examples.

EXAMPLE 1

As noted above, target activated microtransfer is capable of procuring pure populations of cells that are selected according to their expression pattern. These expression patterns may be determined in a complex tissue section using, for example, immunohistochemistry (antibody detetection), or nucleic acid hybridization (with DNA or RNA binding probes). The method disclosed in this example uses standard immunohistochemistry to stain the cells of interest. Once the cells are stained, the tissue section is covered by a clear Ethylene Vinyl Acetate (EVA) film and a laser is then run across the entire tissue section. The areas that are stained absorb the energy locally and melt the EVA film. The film is then lifted off the tissue section, thereby isolating the cells of interest from the remaining tissue section.

Conventional laser-based microdissection depends on the morphological recognition of the desired cells to target them, and can be quite labor intense, particularly if scarce or difficult to dissect cells are targeted. In the present example, the molecule (in this case an antibody) in effect performs the microdissection work for the user, significantly increasing sensitivity and specificity. This example provides a high-throughput method, which is user independent.

Materials and Methods

Immunhistochemistry

Ethanol-Fixed Paraffin-Embedded Tissue

Whole prostate tissue sections were performed and mounted on uncharged slides. Prior to the immunohistochemistry step, the tissue was de-waxed following standard techniques and times: xylene (10 minutes), 100% ethanol (30 seconds), 95% ethanol (30 seconds), 70% ethanol (30 seconds) and deionized water (30 seconds). The DAKO Envision+ System with diaminobenzidine (DAB) (DAKO/Cytomation Inc.) was used as the method for immunohistochemistry, following manufacturer's instructions. However the manufacturer's instructions were changed by making the DAB stain three times as concentrated and the incubation time of the tissue with the DAB stain was extended from 10 minutes to 20 minutes. These modifications produced a darker stain. The slides were not counterstained with hematoxylin to enhance the contrast between stained areas and unstained areas.

Frozen Tissue

A shortened immunohistochemistry protocol was followed for the frozen tissue sections to improve preservation of the RNA and protein quality. Frozen human liver and prostate tissue sections were performed and mounted on uncharged slides. Tissue was fixed with 70% Ethanol for 2 minutes. RNase inhibitor was added to the 70% Ethanol solution to prevent excess degradation. After fixation, the tissue was incubated with the primary antibody for 10 minutes and the secondary antibody polymer (DAKO) for 30 minutes at room temperature. The tissue was washed briefly with 1×PBS pH 7.4 between each step. After color development with the concentrated DAB solution described above, the tissue was washed with $H_2O$ and not counterstained with hematoxylin. The tissue was then dehydrated in graded alcohols (30 seconds each) and xylene (2 minutes) and finally air dried.

Expression Microdissection

An Arcturus PixCell II was used to perform the early target activated microtransfer following standard procedures. The laser was set to the following parameters; Power=100 mW, Duration=30-40 milliseconds, Repeat t=0.2 seconds, Target=0.300 V, Current=25.0 mAmps, Spot Size=30 μm, and Temperature=24° C. (Room Temperature). Once the tissue was covered with the EVA film, the laser was used to irradiate the entire tissue area. Melting was observed only where staining from the immunohistochemistry was located.

Analysis of DNA

Extraction

Procured cells were immediately suspended in 50 μl of buffer containing 0.05 M tris-HCL, 0.001 M EDTA, 1% Tween 20, 0.1 mg/ml proteinase K, pH 8.0 and incubated overnight at 37° C. The mixture was boiled for 10 minutes to inactivate proteinase K and 1.5 μl of this solution was used for PCR.

Primers and PCR Conditions

Analysis was performed using three STS markers (3279, 16152, and 17142 from Research Genetics, Inc) and four polymorphic DNA markers for allelotyping at chromosome 8p21 (D8S136, D8S1836, D8S137 and D8S1733 from Research Genetics, Inc). Reactions were cycled in a Perkin Elmer Cetus thermal cycler using the following conditions: 1 cycle at 94° C. for 10 minutes, 11 cycles of 94° C. for 20 sec, 66° C. for 55 seconds (decreasing 1° C. every cycle), 72° C. for 20 seconds, 29 cycles of 94° C. for 20 seconds, 55° C. for 20 seconds, 72° C. for 20 seconds. PCR was performed in 10 μl volumes and contained 1 μl 10×PCR buffer (100 mM Tris-HCl, pH 8.3; 500 mM KCl; 15 mM $MgCl_2$; 0.1% w/v gelatin; 1.5 μl of DNA extraction buffer; 50 μM of each primer; 20 nM each of dCTP, dGTP, dTTP, and dATP; 0.2 μl [$^{33}$P] dCTP (10 uCi/ul); and 0.1 unit Taq DNA polymerase.

For the STS markers, conditions were similar, except that the corresponding volume of [$^{33}$P] was replaced by DEPC water in the PCR mix and PCR products were electrophoresed in 1.5% agarose gels and visualized with ethidium bromide staining. A negative PCR (no DNA template) was also performed. For allelotyping, labeled amplified DNA was mixed with an equal volume of formamide loading dye (95% formamide; 20 mM EDTA; 0.05% bromophenol blue, and 0.05% xylene cyanol). The samples were denatured for 5 minutes at 94° C. and loaded onto a gel consisting of 6% acrylamide (49:1 acrylamide:bis). Samples were electrophoresed at 1800 volts for 1.5 hours. Gels were transferred to 3 mm Whatman paper, dried, and autoradiography was performed with Kodak X-OMAT film. Loss of hybridization (LOH) was considered with complete or near complete absence of one allele in the tumor DNA as defined by direct visualization.

Analysis of RNA

Extraction

A modified Stratagene RNA Microisolation procedure was used. Samples were immediately suspended in 200 μl of denaturing buffer (4 M guanidium isothiocyanate, 0.02 M Sodium Citrate, 0.5% Sarcosyl, and 0.008 M mercaptoethanol). After phenol/chloroform:isoamyl alcohol (3/1) extraction, RNA was precipitated using 1:1 Vol Isopropanol, and 2 μl Glycogen as carrier. After resuspension of the pellet in 15 μl DECP treated water, samples were DNase treated in using 2 μl Dnase I (Gene Hunter, 10 U/μl), and 2 μl 10× Reaction Buffer (Gene Hunter) and 1 μl RNase inhibitor (Perkin Elmer, 20 U/μl), for 2 hours at 37° C. A re-extraction with phenol/chloroform:isoamyl alcohol (3/1) was performed to remove DNase. The pellet was resuspended in 10 μl DECP treated water and 1 μl RNase inhibitor (Perkin Elmer, 20 U/μl).

Reverse Transcription (RT)

For each sample 2 μl of RNA was used to perform a positive RT and 2 μl to perform a negative RT (no reverse transcriptase). RT was performed using: 2 μl DNase treated RNA, 4 μl 5×RT Buffer (Gene Hunter), 2 μl dNTP (Gene Hunter, 250 μM), 1 μl Random Hexamers (Perkin Elmer, 50 μM), 10 μl of DEPC water. The mixture was incubated 5 minutes at 65° C., 10 minutes at 25° C., 1 μl reverse transcriptase MMLV (Gene Hunter, 0.1 U/μl) was added to the positives samples, 10 minutes at 25° C., 40 minutes at 37° C. and 5 minutes at 94° C.

PCR for β Actin

PCR was performed to analyze RNA quality. Actin primers with a 220 bp product (Clontech) were used as follows: 1 μl cDNA, 1 μl 10×PCR Buffer (Perkin Elmer), 0.8 μl of 10 mM dNTP mix (Gene Hunter, 25 uM), 0.2 μl 20 uM 5' primer, 0.2 μl of 20 uM 3' primer, 0.2 μl Taq Gold (5 U/ul, Perkin Elmer), 6.4 μl DECP water. PCR was performed using the following conditions: 1 cycle of 10 minutes at 94° C., 35 cycles of 45 seconds at 94° C., 45 seconds at 60° C., 45 seconds at 72° C., and 1 cycle of 10 minutes at 72° C.

Electrophoresis

PCR products were electrophoresed in 1.5% agarose gels and visualized with ethidium bromide staining.

Analysis of Protein

Sample Preparation

After expression microdissection, the EVA film (containing the cells of interest) was placed in 50 μl of RIPA buffer with protease inhibitor. Then, 5 μl of 10×SDS loading buffer was added to the sample, in addition to 1 μl of β-mercaptoethanol (βME). The sample was prepared to be loaded on a Tris-Glycine polyacrylamide gel.

Electrophoresis

Twenty microliters of each sample were run on a 4-20% Tris-Glycine gel (Invitrogen) at a constant current of 30 mAmps for ~1 hour. After electrophoresis, the gel was removed from the cassette and stained with SilverQuest Silver Stain (Invitrogen) according to manufacturer's instructions.

Results

FIGS. 9-12 illustrate the successful application of transfer microdissection. FIG. 9 illustrates microdissection of ethanol-fixed whole mount prostate tissue on an uncharged slide, using immunohistochemical identification of the target cells in which the primary antibody used was a Mouse Anti-Human Prostate Specific Antigen (PSA). Positive cells, represented by the dark stain, are shown in FIG. 9A. The same area of the tissue after target-activated microtransfer is shown in FIG. 9B. The laser irradiated the entire tissue area, yet only the stained specific cell population was procured by removing the EVA film from the irradiated sample. FIG. 9C illustrates an image of the EVA film after microdissection, in which the target cells are adhered to the film. In FIG. 9D, arrows point to basal cells that remain after microdissection. Target-activated microtransfer allows for the selection of cellular subtypes, such as the procurement of secretory and not basal cells from among epithelial cells, as shown in FIG. 9D in which the basal cells remain after transfer of the secretory cells.

Figure 10B:
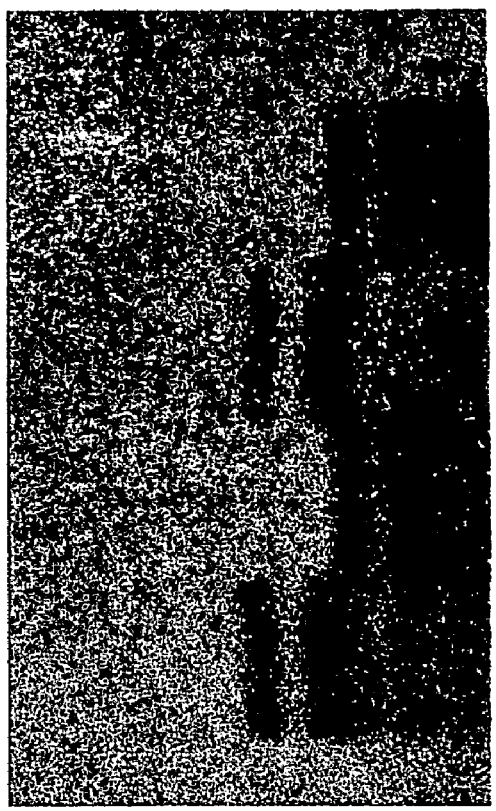
FIG. 10B illustrates amplification of microsatellites (polymorphic markers) for allelotyping, which is useful for loss of heterozygosity (deletion) analysis.
Figure 10A:
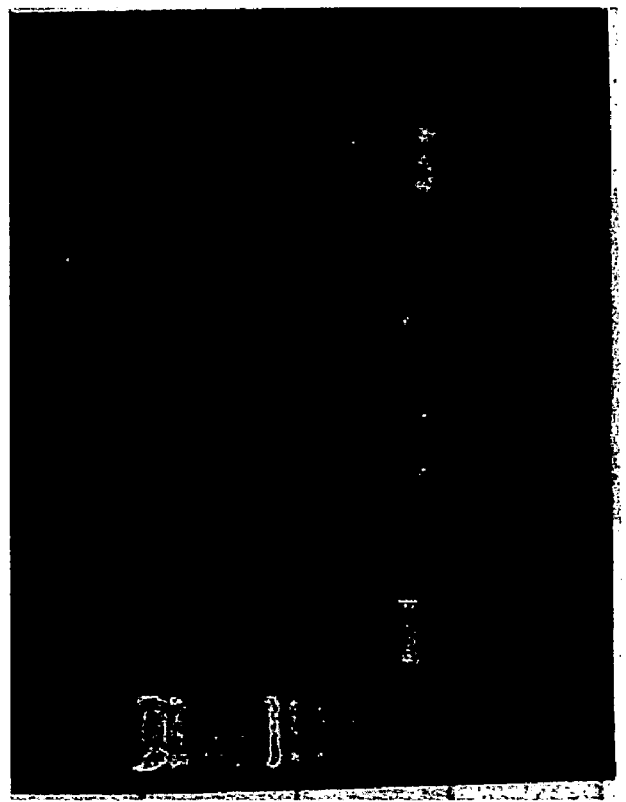
FIG. 10A illustrates DNA amplification using amplification of Sequence Tagged Site (STS) markers (non-polymorphic genomic DNA markers), which is useful in cloning studies.
Figure 11:
FIG. 11 illustrates amplification of nucleic acids procured from microdissected cells for gene expression analysis. RT-PCR from procured RNA allows for amplification of specific genes to assess their level of expression among the microdissected cells.

FIG. 10A shows the results of DNA amplification using amplification of Sequence Tagged Site (STS) markers (non-polymorphic genomic DNA markers). Analysis of STS markers are a useful tool for cloning studies. FIG. 10B shows amplification of microsatellite (polymorphic markers) for allelotyping, important for Loss of Heterozygosity (deletion) analysis FIG. 11 illustrates gene expression analysis performed with RNA from microdissected cells. Lane 1=negative control, Lane 2=Target-activated Microtransfer of Cytokeratin positive cells, Lane 3=positive control. Reverse transcription allows for amplification of specific genes to assess their level of expression among the microdissected cells. Optimizing the method for superior preservation of global RNA integrity allows high throughput RNA analysis studies, such as microarray analysis of target activated microtransfer cells.

Figure 12:
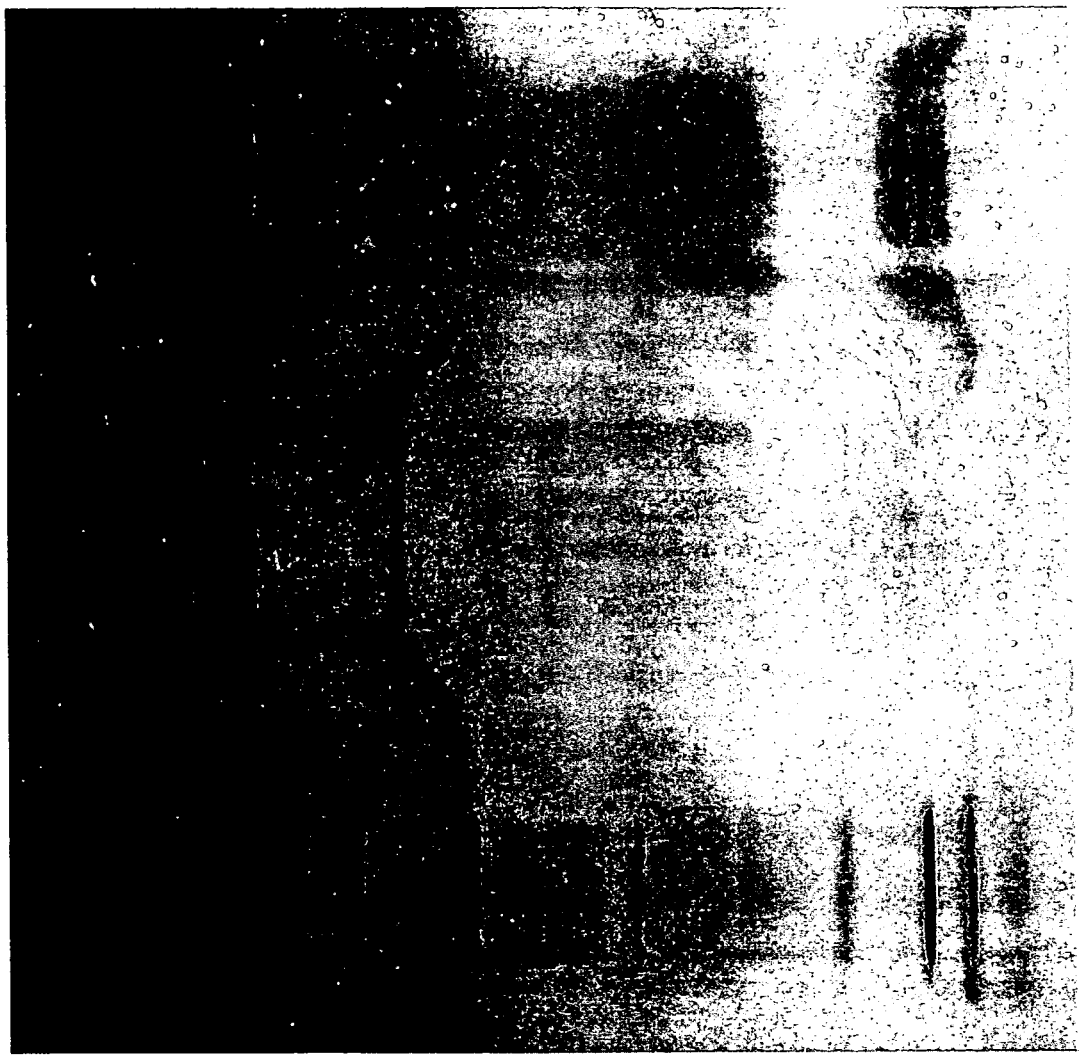
FIG. 12 is a digital image of a silver stained one-dimensional tris-glycine polyacrylamide gel of proteins from human liver tissue. Lane 1=Molecular Weight Marker, Lane 2=Proteins from a lysed sample of target-activated microtransfer of GAPDH positive cells, Lane 3=Proteins lysed from the remaining tissue. The difference in intensity and number of bands detected between Lane 2 and Lane 3 is due to the amount of cells microdissected compared to an entire tissue scrape.

FIG. 12 illustrates protein analysis of human liver tissue cells, as shown in a silver stained one-dimensional Tris-Glycine polyacrylamide gel. Lane 1=Molecular Weight Marker, Lane 2=Proteins from a lysed sample of target-activated microtransfer of GAPDH positive cells, Lane 3=Proteins lysed from the remaining tissue. Western blotting can be performed to assess expression of single proteins using these samples.

Additional aspects of the disclosed methods are discussed in the following examples.

EXAMPLE 2

Automated Scanning

Target activated microtransfer was performed using a 400 mW fiber optic LD diode source in the continuous mode to scan the bottom of an immunostained prostate tissue section. The fiber of the light source was in contact with the lower glass surface of the slide, while the tissue was mounted on the top glass surface. A large sheet of clear Elvax510 EVA on top of the tissue served as the transfer film. The fiber provided a 200 μm spot on the tissue section, and was scanned at ~3 cm/sec across the lower surface of the slide to achieve fusion and specific microtransfer of target.

Microtransfer can be automated in this fashion, for example by using a programmable stage to move the tissue or a laser scanner relative to the slide. This programmed or predetermined movement sweeps the laser beam across the tissue, allowing the entire slide to be irradiated in ~1 minute.

Many other laser sources could be used for this purpose, such as a 1 W argon laser. The blue/green light would be expected to be particularly efficient. The speed of scanning the entire slide would be expected to increase linearly with increasing laser power.

EXAMPLE 3

Examples of Tested Targets

A variety of different primary antibodies were tested in the disclosed microdissection/microtransfer method to demonstrate the general applicability of the method to a variety of different targets. Antibodies tested include: Cyokeratin AE1/AE3; LP34 (Cytokeratin, Basal Cells; CD34; CD3; PSA; Desmin; E-cadherin; S-100; GAPDH; CD45RO; Histone; Vimetin; and Actin.

All of these antibodies provided specific activation and adherence to the transfer layer, with no melting observed in unstained areas.

EXAMPLE 4

Triggering Events

As used herein, the term "triggering event" or "trigger" refers to an event that affects the reagent, such that the reagent alters or activates the transfer surface to permit selective removal of the target from the biological sample. As noted above, the change in the transfer surface may cause focal adherence to the transfer film by direct activation of the activating moiety, for example by using a light source to activate an absorbing activating moiety to cause that moiety to fluoresce and release heat to adhere the target to the transfer surface. Alternatively, activation involves adding a substrate, such as a substrate required by a heat-generating enzyme to produce heat. In some examples, activation involves more than one step, for example supplying a substrate for an enzyme to deposit a precipitate in the target, then illuminating the targets to heat them. Contemplated triggers include (but are not limited to) electromagnetic radiation sources, other radiation sources (such as ionizing radiation), electrically heated radiation heaters, heated probes, and focused or masked non-laser light sources such as flashbulbs, and xenon lamps.

In particular examples, the stimulus (such as a laser or electromagnetic source) is applied in a manner that activates the activating moiety without directly melting the plastic of the transfer layer. For example, when the activating moiety contains a chromophore, the illumination is selected (for example by the placement of filters) to be at a wavelength that is absorbed by the chromophore but is substantially not absorbed by the transfer layer. Minimizing absorption of light energy by the transfer layer reduces non-specific heating of that layer which can adhere the transfer layer to non-target regions of the biological sample.

In certain examples, the trigger is exposure to electromagnetic radiation from a laser, which can be non-specifically scanned over the entire tissue section (or particular regions of the tissue section) to activate the reagent. Alternatively, the laser can be directed at the target under microscopic visualization, as in laser capture microdissection (LCM). Although selecting the targets and directing the laser at them is not necessary with the target activated transfer methods disclosed herein, because of the "self-selection" of the targets, directing the laser at the target can still be combined with target actuated transfer. Even though this approach avoids one of the advantages of target activated transfer (no necessity to visualize the target), the in situ signal provided by the stimulated activating moiety is still an effective way to form a target-specific bond with the transfer substrate even when using visual localization and activation. Suitable lasers for these purposes include any laser source with sufficient pulse energy output at a wavelength efficiently and selectively absorbed by the target tissue. Visible and near-infrared laser diodes are an extremely durable, low-cost, and low footprint approach, but a very broad range of lasers with pulse outputs in the range of 1-100 µJ in less than 50 msec are additional examples of lasers that could be used. Lasers having wavelength outputs from ultraviolet to infrared can be used according to the present disclosure, provided that suitable materials are used.

In one embodiment, the laser is a rapidly scanned continuous wave laser in which 1-100 µJ is delivered to each target area depending on the size of the scanned beam (i.e, increasing power with increasing target size). For example the laser diode with wavelengths between 690 and 1300 nm could be scanned rapidly over target regions rather than pulsed. In a broad wavelength range, conventional glass microscope optics are highly transmissive and can be used to focus the laser. In some embodiments, the wavelengths used for laser activation and film absorption are chosen outside the normal range used for microscopic imaging. Reproducible microtransfer of tissue can be obtained using a variety of infrared wavelengths from the laser.

EXAMPLE 5

Transfer Substrates

The transfer substrates can be made of a variety of materials that are suitable for selective removal of targets from biological samples. In some instances, the material is transparent or translucent, to allow visualization (such as microscopic examination) of the components underneath the transfer substrate. In examples in which the transfer substrate melts and fuses with the underlying target, the substrate is made of a material that can change its shape and/or adhesiveness in response to the trigger. For instance, it is made of a thermoplastic material that partially melts and flows against or around the target. Cells adherent to the transfer substrate retain their morphologic features, and the process of adherence to a transfer substrate does not damage them (or biomolecules which they contain) because the transfer substrate absorbs the energy of the stimulus.

Transfer substrates may be permanently bonded to a fixed surface (e.g., vial cap), to facilitate automated application of a transfer substrate to a fixed sample. Examples of transfer substrate for use with the disclosure include (but are not limited to) emulsion layers, coated films, and separate impregnated webs fixed to a backing layer. In certain disclosed embodiments, thermoplastic polymer films are used as transfer substrates. Such polymer films may be transparent or translucent to visible light for use with conventional light microscopy and absorb weakly, if at all, at the microscopy visualization wavelength but strongly at specific regions of the electromagnetic spectrum (for example in regions of the infrared associated with strong molecular vibration modes such as 3000, 1800, 1400-960 $cm^{-1}$).

Transfer films suitable for use in target activated transfer may be made of a wide variety of electromagnetically or thermally activatable materials, such as ethylene vinyl acetate (EVA), polyurethanes, polyvinyl acetates, and the like. Specific other selectively activatable materials found useful in the methods of the disclosure are: thermal sensitive adhesives and waxes, such as Precision Coatings product #HAL-2 180C; thermally-activated hot glues and sealants, such as those from Ban Fastening Systems (Brooklyn, N.Y.); ultraviolet sensitive or curing optical adhesives, such as ThorLabs, Inc. product N060-N0A81; thermal or optical emulsions, such as silk-screen coated emulsion B6, high mesh powdered, reconstituted lelt fixit emulsion (Riso Kagaku Corp.) and various other compounds including acetal, acrylic, alloys and blends, allyl, bismaleimides, cellulosics, epoxy, fluoroplastics, ketone-based resins, liquid crystal polymers, melamine-formaldehyde, nitrile, nylon, phenolic, polyamide, polyacrylate, polybenzimidazole, polybutylene, polycarbonate, thermoplastic polyester, liquid crystal polymers, polybutylene terephthalate (PBT), polycyclohexvlenedimethylene terephthalate (PCT), engineering grade polyethylene terephthalate (PET), standard grade polyethylene terephthalate (PET), thermoset polyetherimide polyethylene polyester, branched polyethylene, ethylene acid copolymer, ethylene-ethyl acrylate (EEA), ethylene-methyl acrylate (EMAC), ethylene-vinyl alcohol copolymers (EVOH), high-density polyethylene, HMW-high-density polyethylene, Ionomer, linear low-density polyethylene, linear polyethylene, low-density polyethylene, UHMW polyethylene, very low-density polyethylene, thermoplastic polyimide, thermoset polyimide, polymethylpentene, modified Polyphenylene oxide, polyphenylene sulfide, blow molding PPS, polyphthalamide, polypropylene, polypropylene homopolymer, polypropylene impact copolymers, polypropylene random copolymers, silicones, styrenic resins, ABS, ACS, acrylic-styrene-acrylonitrile, expandable polystyrene, general purpose polystyrene, impact polystyrene, olefin-modified SAN, polystyrene, styrene-acrylonitrile (SAN) and styrene-butadiene copolymers.

Although the transfer substrates are depicted in FIGS. 1-5 as being a single layer, the transfer substrate can instead be a multi-layered member as shown in FIGS. 8A-8D. In the example of target activated transfer shown in FIG. 8, transfer substrate 200 includes a backing layer 202 and an activatable layer 204 that can be activated to become adhesive. The backing layer 202 is preferably transparent, for example made of a transparent polymer, glass, or similar material. The activatable layer 204 can be an emulsion layer, a coated film, or a separate impregnated web fixed to backing layer 202. The backing layer 202 provides physical support for the adhesive surface, and thus can be integrated physically into the activatable adhesive surface.

Figure 8A:
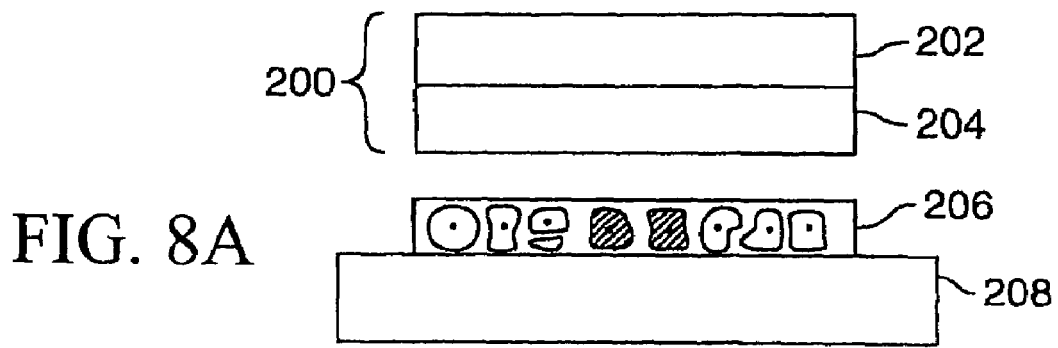
FIGS. 8A-8D are schematic illustrations of the sequential steps of an adhesive transfer method according to one embodiment of the method in which the transfer substrate is a multi-layered member.

As depicted in FIG. 8A, the transfer substrate 200 is initially positioned over a cellular material sample 206 which can be a microtome section or cell smear that is supported on a support member 208, which can be a microscopic slide. In the case of a tissue microtome, routine procedures can be used to provide paraffin embedded, formalin-fixed tissue samples.

Figure 8B:
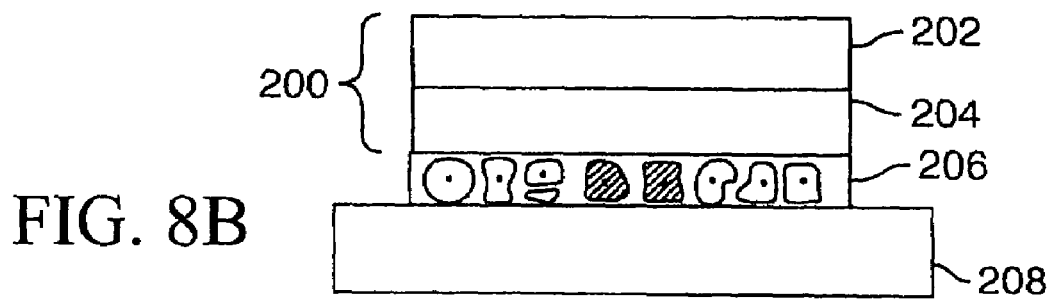
Figure 8C:
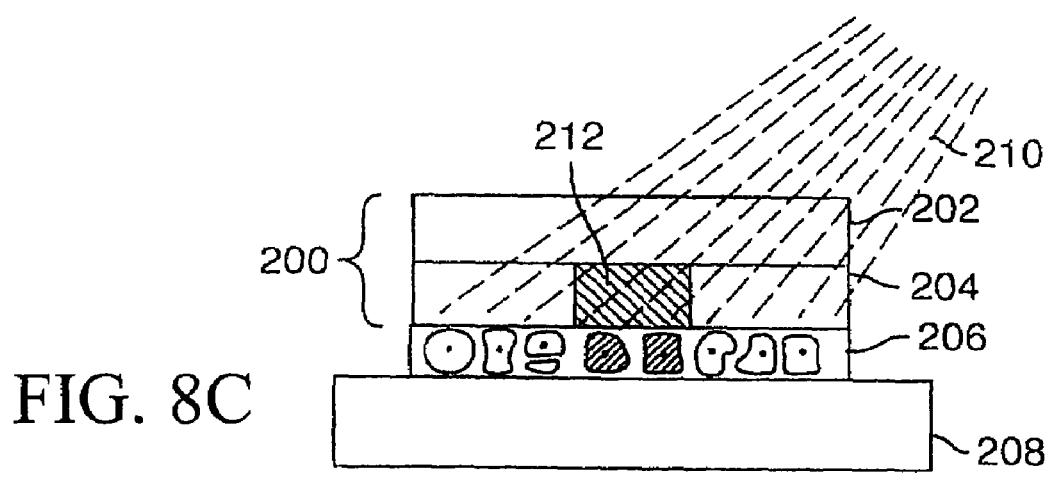

As shown in FIG. 8B, the transfer substrate 200 is brought into contact with the cellular material sample 206. It is noted that the activatable layer 204 preferably has a larger surface area than the subregion of the tissue sample that is subsequently selected for procurement. Within sample 206 are shown two cells (shaded) to which an immunofluroescent reagent (not shown) has selectively bound. After the transfer surface 204 is brought into contact with the sample 206, the reagent is activated by exposing sample 206 to a source of light 210, which illuminates the target cells and immunoflourescent reagent, and heats an overlying segment 212 of sample 206. This target region can range in size from an area smaller than a single cell (less than 10 microns), to single cell or a few cells, to a whole field of cells or tissue. After the segment 212 is heated, that segment adheres to the target cells (which are collectively identified as target "A" in FIG. 8D). Although FIGS. 8C and 8D depict a single target region "A", it is to be understood that multiple, discontinuous regions of interest could be present throughout sample 206.

Figure 8D:
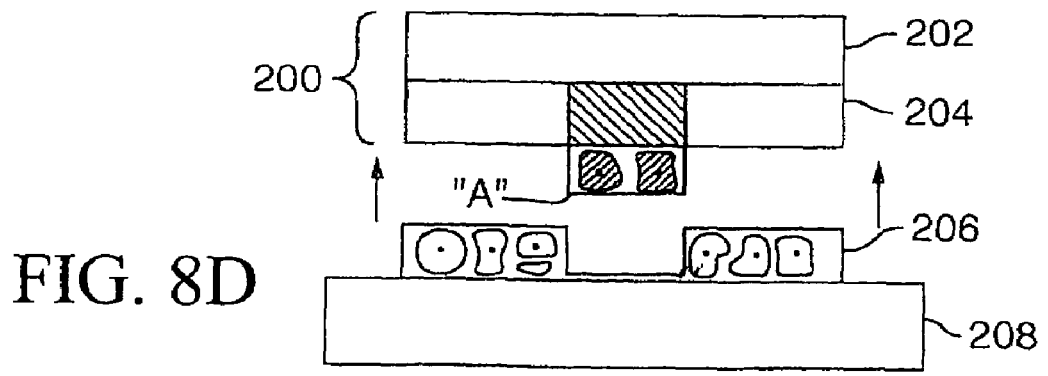
Figure 9A:
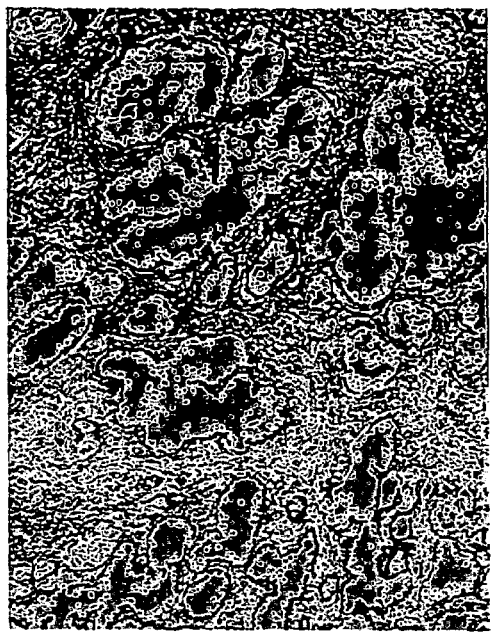
FIGS. 9A-9D are digital images that sequentially illustrate target activated microtransfer of prostate cells from a whole mount ethanol-fixed prostate tissue sample. The primary antibody used was a Mouse Anti-Human Prostate Specific Antigen (PSA). Positive cells are seen in FIG. 9A, while FIG. 9B demonstrates the same area of tissue after target activated microtransfer.
Figure 9B:
Figure 9C:
Figure 9D:

As depicted in FIG. 8D, after one or more target regions "A" are adhered to transfer substrate 200, the transfer substrate 200 is detached from the sample support 208. As shown, the removed transfer substrate 200 carries with it only the precise cellular material from the region of interest "A", which is pulled away from the remaining cellular material sample. As illustrated in FIG. 8D, the region of interest "A" contains the cells of interest as well as some other surrounding material from sample 206.

EXAMPLE 6

Examples of Activating Moieties of Reagents

The activating moieties of the reagents that specifically bind to the target can include luminescent agents, such as a fluorophore. Luminescence is the emission of visible or invisible radiation as a result of absorption of exciting energy in the form of photons, charged particles, or chemical change. It is a general term that includes both fluorescence and phosphorescence. An example of a luminescent molecule includes, but is not limited to, aequorin (Tsien, 1998, Ann. Rev. Biochem. 67:509). A fluorophore is a chemical compound that, when excited by exposure to a particular wavelength of light, emits light (fluoresces), for example at a different wavelength than that to which it was exposed. Fluorophores can be described in terms of their emission profile, or "color." Green fluorophores, for example Cy3, FITC, and Oregon Green, are characterized by their emission at wavelengths generally in the range of 515-540 nm ($\lambda$). Red fluorophores, for example Texas Red, Cy5 and tetramethylrhodamine, are characterized by their emission at wavelengths generally in the range of 590-690 nm ($\lambda$).

Examples of fluorophores include: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other fluorophores include thiol-reactive europium chelates that emit at approximately 617 nm (Heyduk and Heyduk, Analyt. Biochem. 248:216-227, 1997; J. Biol. Chem. 274:3315-3322, 1999); cyanine, merocyanine, styryl, and oxonyl compounds, such as those disclosed in U.S. Pat. Nos. 5,268,486; 5,486,616; 5,627,027; 5,569,587; and 5,569,766, and in published PCT patent application no. US98/00475. Specific examples of fluorophores disclosed in one or more of these patent documents include Cy3 and Cy5. Other fluorophores include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores are known to those skilled in the art, for example those available from Molecular Probes (Eugene, Oreg.).

Particularly useful fluorophores have the ability to be attached to (coupled with) a nucleotide or a protein, such as a modified nucleotide or protein, are substantially stable against photobleaching, and have high quantum.

EXAMPLE 7

Reagents that Include a Targeting Moiety and an Activating Moiety

The reagents used in the target activated transfer methods may be constructed to combine at least two functional domains, or "moieties" in a single molecule, such that application of separate components is not necessary. The moiety that targets the reagent to a target is referred to as the targeting domain or "targeting moiety," while the "activating moiety" acts upon the transfer surface to focally change it (for example by fusing to it) to allow selective removal of the target from the biological sample.

The two moieties of such a reagent are assembled in any order, or can each be linked independently to a separate linker molecule (such as a chemical crosslinker, a polymer complex, etc.). The domains need not be organized in a specific order (e.g., the targeting and active moieties can be either the amino-proximal domain of a protein molecule or the 3' end of a molecule). For instance, in some embodiments, multiple active and/or targeting moieties can be joined to a single polymer, or can be directly joined to each other (as in FIG. 6D).

It is specifically contemplated that the reagents can be fusion molecules that contain multiple copies of active moieties, and/or multiple copies of targeting moieties. The construction of chimeric recombinant molecules as fusion proteins from domains of known proteins is well known. In general, nucleic acid molecules that encode the desired molecule are joined using standard techniques to create a single, operably linked fusion polynucleotide, including recombinant DNA techniques. Molecular biological techniques may be found in Sambrook et al. (In *Molecular Cloning: A Laboratory Manual*, Cold Spring Harbor, N.Y., 1989).

By way of example, the reagent is created using recombinant techniques by cloning nucleic acid sequences encoding a protein or nucleic acid polymer and/or linkers, a targeting moiety, and an activating moiety, into an expression vector. Following induction of the expression vector, a nucleic acid is synthesized and purified using techniques known to those of skill in the art, such as those found in Sambrook et al. (In *Molecular Cloning: A Laboratory Manual*, Cold Spring Harbor, N.Y., 1989). In some embodiments, the targeting moiety is a single-chain antibody. Although the H and L chains of an Fv fragment are encoded by separate genes, a synthetic linker can be made that enables them to be made as a single protein chain by recombinant methods; see Bird et al. Science 242: 423-426, 19888; and Huston et al. PNAS 85: 5879-5883, 1988).

Alternatively, the reagent may be synthesized using traditional chemical synthesis techniques, as found in Foulon et al., *Bioconjug Chem*, 10(5): 867-76, 1999.

Although the reagents are not limited to any particular embodiment, a specific example of one particular reagent is shown in the incorporated PCT/US03/12734.

EXAMPLE 8

Selection of Targeting Moieties

Targeting moieties are selected in response to the nature of the target. For example, essentially any cell type is suitable for targeting, where a molecule is known or can be identified that is suitable as a cell-specific target molecule to which the targeting moiety can be directed. A targeting molecule can be applied to various types of samples, for instance to a tissue section mounted on a standard glass histopathology slide, tissue arrays, or to cells otherwise cultured on an amenable medium.

Certain embodiments use antibodies (or fragments thereof) as targeting moieties. In some embodiments, the targeting moiety is an antibody (such as rabbit anti-goat IgG) directed to bind an antibody bound to a specific protein in a tissue preparation. In such embodiments, it is possible to differentiate pure populations of immunotypically-defined cells from a sea of similar appearing cells, and procure such cells for further analysis. By way of example, the targeting moiety is a monoclonal antibody specific to a tumor marker (such as Cyclin D1/D2/D3 antibodies, Melanoma Associated Antigen).

In certain embodiments, the reagent is an enzyme-linked immunoreagent that deposits an absorptive precipitate (such as an inorganic phosphate precipitate) selectively in cells of interest upon exposure to a substrate. In such embodiments, the antigen that is the target of the targeting moiety is either solely expressed by the cells of interest, or is expressed at a higher level in the cells of interest, such that the expressing cells can be sufficiently differentiated from non-expressing cells by the absorptive precipitate. For example, cells expressing antigens or sufficiently higher numbers of antigens than background cells will have an optical density (OD) of at least about 0.2-0.6, such that the precipitate will efficiently absorb the energy of the stimulus (such as a flash lamp), causing sufficient local heating of the target to cause it to adhere to a transfer film. The reaction that deposits the precipitate can be continued until the local absorption at sites of high antibody binding is about 20-90% of the incipient light.

A targeting moiety that is an antibody can optionally be a secondary antibody that binds to a previously and separately applied primary antibody. Thus, a user can select a primary antibody specific to certain types of cells (such as goat anti-mouse IgG, rabbit anti-lactoperoxidase IgG, etc.) and apply a broad-spectrum reagent containing a secondary antibody designed to detect the primary antibody (for example HRP-conjugated rabbit anti-goat IgG or HRP-conjugated mouse anti-rabbit IgG), which allows the user to procure cells selected by the specificity of the primary antibody. In this example, the secondary antibody is a general or broad spectrum targeting moiety, which is useful in procuring cells or cellular components from samples in which the primary antibody binds. The secondary antibody is an example of a standardized reagent that is not specific to the target, but instead recognizes antibodies that are specific to the target. The "targeting moiety" in this instance includes both the primary and secondary antibodies.

Fluorescent primary antibodies that specifically bind to certain antigenic molecules, such as particular proteins or carbohydrates, are available commercially from many sources including Molecular Probes, Inc. (Eugene, Oreg.) and BAbCo (Richmond Calif.). Currently unavailable monoclonal or polyclonal antibodies against a particular antigen, such as a particular protein, may also be produced using methods well known in the art, and subsequently conjugated with a fluorescent moiety.

In some embodiments, the targeting moiety is a hapten, a lectin, a carbohydrate, a cofactor, a receptor ligand, or a protein with high specificity for a binding partner, such as the biotin/(strept)avidin binding pair, or protein A or G.

Fluorescent specific binding lectins are proteins that bind specifically to certain configurations of sugar molecules. Lectins may be used to identify cells and tissues based upon the presence of particular proteoglycans, glycoproteins, and glycolipids on their surface. Conjugates of protein A and protein G are bacterial proteins that bind with high affinity to the Fc portion of various classes and subclasses of immunoglobulins from a number of species. Such conjugates are available from Molecular Probes, Inc. (Eugene, Oreg.).

In other embodiments, a probe or short DNA sequence serves as the targeting moiety, and binds to a complementary molecule or sequence (such as expressed transcription factor or DNA regulatory sequence) within the target cells. In certain embodiments, the complementary sequence is present as a result of ongoing transcription within the cell. These embodiments may be used to profile the response of target cells to internal or external conditions (such as treatments with pharmaceuticals, onset of disease, etc.).

EXAMPLE 9

Selection of Activating Moiety

The choice of an activating moiety for incorporation into the reagent may be influenced by the method(s) of inducing the alteration of the transfer surface, for example whether the alteration will be adherence of transfer substrate to the target, or induction of a focal change of permeability of the transfer substrate to the target.

Examples of activating moieties that absorb light to heat the transfer surface include infrared absorbing dyes, which provide strong absorption at other specific infrared wavelengths. Many dye types are suitable for IR absorption, as most classes of visible absorbing dyes can be extended in wavelength by molecular modification. Phthalocyanines and cyanines provide the advantages of stability, ease of preparation, solubility, optical and other properties. Moreover, such dyes are highly chemically modifiable (see *Infrared Absorbing Dyes*, Masaru Matsuoka, ed. (U. of Osaka, Sakai, Osaka, Plenum Press NY 1990; available in the NBS library series: Topics in Applied Chemistry, A. R. Katritzky and G. J. Sabong, eds.). Example phthalocyanine dyes suitable for use as activating moieties can be found in the Aldrich Chemical Catalog, and some of them are listed in Table 1.

TABLE 1

PHTHALOCYANINE DYES (Aldrich Chemical Company)

| # | Name |
|---|---|
| #412066 | Name: TETRAKIS (4-CUMYLPHENOXY)PHTHALOCYANINE, 97% |
| #404543 | Name: TIN(II) PHTHALOCYANINE |
| #406481 | Name: SILICON PHTHALOCYANINE DIHYDROXIDE |
| #414387 | Name: VANADYL 2,9,16,23-TETRAPHENOXY-29H,31H-PHTHALOCYANINE |
| #393932 | Name: MANGANESE(III) PHTHALOCYANINE CHLORIDE |
| #410160 | Name: IRON(II) PHTHALOCYANINE BIS (PYRIDINE) COMPLEX |
| #404551 | Name: TITANYL PHTHALOCYANINE |
| #418145 | Name: 1,8,15,22-TETRAPHENOXY-29H,31H-PHTHALOCYANINE |
| #418153 | Name: 2,9,16,23-TETRAPHENOXY-29H,31H-PHTHALOCYANINE |
| #379573 | Name: IRON(III) PHTHALOCYANINE CHLORIDE |
| #406473 | Name: TIN(IV) PHTHALOCYANINE DICHLORIDE |
| #415448 | Name: NICKEL(II) TETRAKIS(4-CUMYLPHENOXY)-PHTHALOCYANINE |
| #418161 | Name: 1,8,15,22-TETRAKIS(PHENYLTHIO)-29H,31H-PHTHALOCYANINE |
| #418188 | Name: 2,9,16,23-TETRAKIS(PHENYLTHIO)-29H,31H-PHTHALOCYANINE |
| #408808 | Name: GALLIUM(III) PHTHALOCYANINE CHLORIDE |
| #418986 | Name: ALUMINUM 2,9,16,23-TETRAPHENOXY-29H,31H-PHTHALOCYANIN |
| #310204 | Name: COPPER(II) 4,4',4'',4'''-TETRAAZA-29H,31H-PHTHALOCYAN |
| #402737 | Name: MAGNESIUM PHTHALOCYANINE |
| #402745 | Name: DISODIUM PHTHALOCYANINE |
| #418250 | Name: ALUMINUM 2,9,1 |
| #341169 | Name: ZINC PHTHALOCYANINE |
| #379557 | Name: MANGANESE(II) PHTHALOCYANINE |
| #414379 | Name: NICKEL(II) 2,9,16,23-TETRAPHENOXY-29H,31H-PHTHALOCYAN |
| #433462 | Name: METHYLSILICON |
| #418234 | Name: ZINC 2,9,16,23-TETRAKIS(PHENYLTHIO)-29H,31H-PHTHALOCY |
| #418242 | Name: ALUMINUM 1,8,1 |
| #379549 | Name: IRON(II) PHTHALOCYANINE |
| #408875 | Name: LEAD(II) TETRAKIS (4-CUMYLPHENOXY) PHTHALOCYANINE |
| #393894 | Name: VANADYL 3,10,17,24-TETRA-TERT-BUTYL-1,8,15,22-TETRAKI |
| #432946 | Name: COPPER(II) TET |
| #441082 | Name: GALLIUM(III) P |
| #423157 | Name: 2,9,16,23-TETR |
| #393886 | Name: COPPER(II) 3,10,17,24-TETRA-TERT-BUTYL-1,8,15,22-TETR#418269 Name: ALUMINUM 1,8,1 |
| #423165 | Name: COPPER(II) 2,9 |
| #430994 | Name: ZINC 2,9,16,23 |
| #307696 | Name: COBALT(II) PHTHALOCYANINE |
| #432180 | Name: SILICON 2,9,16 |
| #432180 | Name: SILICON 2,9,16 |
| #446637 | Name: ALUMINUM PHTHA |
| #253103 | Name: 29H,31H-PHTHALOCYANINE, 98% |
| #379565 | Name: LEAD(II) PHTHALOCYANINE |
| #418277 | Name: ALUMINUM 2,9,1 |
| #362530 | Name: ALUMINUM PHTHALOCYANINE CHLORIDE |
| #444529 | Name: ZINC 1,2,3,4,8 |
| #452521 | Name: IRON(III) PHTH |
| #446645 | Name: COBALT(II) 1,2 |
| #446653 | Name: COPPER(II) 1,2 |
| #446653 | Name: COPPER(II) 1,2 |
| #448044 | Name: IRON(II) 1,2,3 |
| #448044 | Name: IRON(II) 1,2,3 |
| #386626 | Name: ALUMINUM 1,4,8,11,15,18,22,25-OCTABUTOXY-29H,31H-PHTH |
| #360635 | Name: NICKEL(II) PHTHALOCYANINE |
| #448311 | Name: COPPER(II) 1,2 |
| #428159 | Name: SILICON(IV) PH |
| #386618 | Name: COPPER(II) 1,4,8,11,15,18,22,25-OCTABUTOXY-29H,31H-PH |
| #287768 | Name: SILICON PHTHALOCYANINE DICHLORIDE |
| #408883 | Name: NICKEL(II) 1,4,8,11,15,18,22,25-OCTABUTOXY-29H,31H-PH |
| #383813 | Name: ZINC 1,4,8,11,15,18,22,25-OCTABUTOXY-29H,31H-PHTHALOC |
| #362549 | Name: DILITHIUM PHTHALOCYANINE |
| #383805 | Name: 1,4,8,11,15,18,22,25-OCTABUTOXY-29H,31H-PHTHALOCYANIN |
| #252980 | Name: COPPER(II) PHTHALOCYANINE |
| #245356 | Name: COPPER(II) PHT |

Near-IR absorbing dyes are also suitable for use as activating moieties. For example, Aldrich #22886-9 dye, indocyanine green, and Aldrich #11991-1, naphthol green B, are suitable. Particular embodiments use the naphthalocyanine dyes, which have low water solubility but high solubility in non-polar polymers. For example, vanadyl 5,14,23,32-tetraphenyl 2,3-naphthalocyanine [Aldrich 39, 317-7 (CA 131220-68-3)] with a molecular formula weight of 1084 daltons exhibits a strong absorption peak (with a molar extinction coefficient of 200,000 at 846 nm) and high solubility in ethylene vinyl acetate (EVA) low melting polymers (such as Dupont ELVAX™. 410). This dye absorption peak matches well the emission wavelength of selected GaAlAs laser diodes. Similarly, vanadyl 2,11,20,29-tetra-tert-butyl-2,3-naphthalocyanine [CA 105011-00-5] FW1004 absorbs near IR with a narrow peak at 808 nm, which closely matches the emission wavelength (selected by choosing a different value of [A1]) of GaAlAs laser diodes widely used to pump solid state Nd:YAG lasers. All these naphthalocyanine dyes (see Table 2 below) are highly soluble in EVA polymer thermoplastics and other similar thermoplastic materials. They are quite stable compounds particularly with heating to ~300° C. and do not exhibit adverse photochemistry which might affect biological macromolecules in the tissue.

Laser light absorbing, heat generating naphthalocyanine dyes that are suitable as activating agents are presented in the Aldrich Catalog and include:

TABLE 2

NAPHTHALOCYANINE DYES (Aldrich Chemical Company)

vanadyl 5,14,23,32-tetraphenyl 2,3-naphthalocyanine;
Aldrich 39, 317-7CA 131220-68-3FW1084 846 nm
tin(IV) 2,3-naphthalocyanine dichloride;
Aldrich 40, 651-1CA 26857-61-4 FW902 828 nm
silicon(IV) 2,3-naphthalocyanine dihydroxide;
Aldrich 40, 653-8CA 92396-90-2 FW775 785 nm
silicon(IV) 2,3-naphthalocyanine dioctyloxide;
Aldrich 40, 767-4CA 92941-50-9 FW941 798 nm
5,9,14,18,23,27,32,36-octabutoxy 2,3-naphthalocyanine;
Aldrich 41, 207-4CA 105528-25-4FW1292 867 nm
copper(II) 5,91,14,18,23,27,32,36-octabutoxy 2,3-naphthalocyanine;
Aldrich 41, 528-6CA 155773-67-4FW 853 nm
nickel(II) 5,9,14,18,23,27,32,36-octabutoxy-2,3-naphthalocyanine;
Aldrich 41, 885-4CA 155773-70-9FW1348 848 nm
vanadyl 2,11,20,29-tetra-tert-butyl-2,3-naphthalocyanine;
Aldrich 43, 296-2CA 105011-00-5FW1004 808 nm
nickel(II) 5,9,14,18,23,27,32,36-octabutoxy-2,3-naphthalocyanine;
Aldrich 41, 885-4CA 155773-70-9FW1348 848 nm
vanadyl 2,11,20,29-tetra-tert-butyl-2,3-naphthalocyanine;
Aldrich 43, 296-2CA 105011-00-5FW1004 808 nm Indicators may also be included, either in the transfer substrate or in a separate layer or layers, to define the location of adhesion of cells or cellular components. Such indicators include thermochromic dyes, dye precursors that combine upon melting to form a color for visible or instrumental identification, and dyes that are converted to color by other effects of optical absorption. Suitable indicators also include other physical effects, such as the appearance or disappearance of translucency or opacity upon optical exposure or upon heating.

In some embodiments, selective transfer of components from a tissue section to a Layered Expression Scan (LES) substrate may be accomplished (as disclosed in WO 02/10751, which is incorporated by reference) by covering a tissue section with an impermeable or semi-permeable photodepolymerizable polymer, photodepolymerizing the polymer over desired portions of the tissue section, removing the photodepolymerized polymer to create "holes" over the cells of interest, and transferring the contents of the cells of interest into the substrate.

Methods for selectively depolymerizing a polymer layer over desired cells are disclosed in U.S. Pat. No. 6,087,134 to Saunders. Photodepolymerizable polymers include quinone diazides, novalak resins, and acrylics. Additional materials that are photodepolymerizable are disclosed in C. G. Roffey, *Photopolymerization of Surface Coatings*, John Wiley & Sons, 1982 and in W. Schnabel, *Polymer Degradation*, Hanser Int., 1981.

EXAMPLE 10

Linker Molecules

Figure 6:
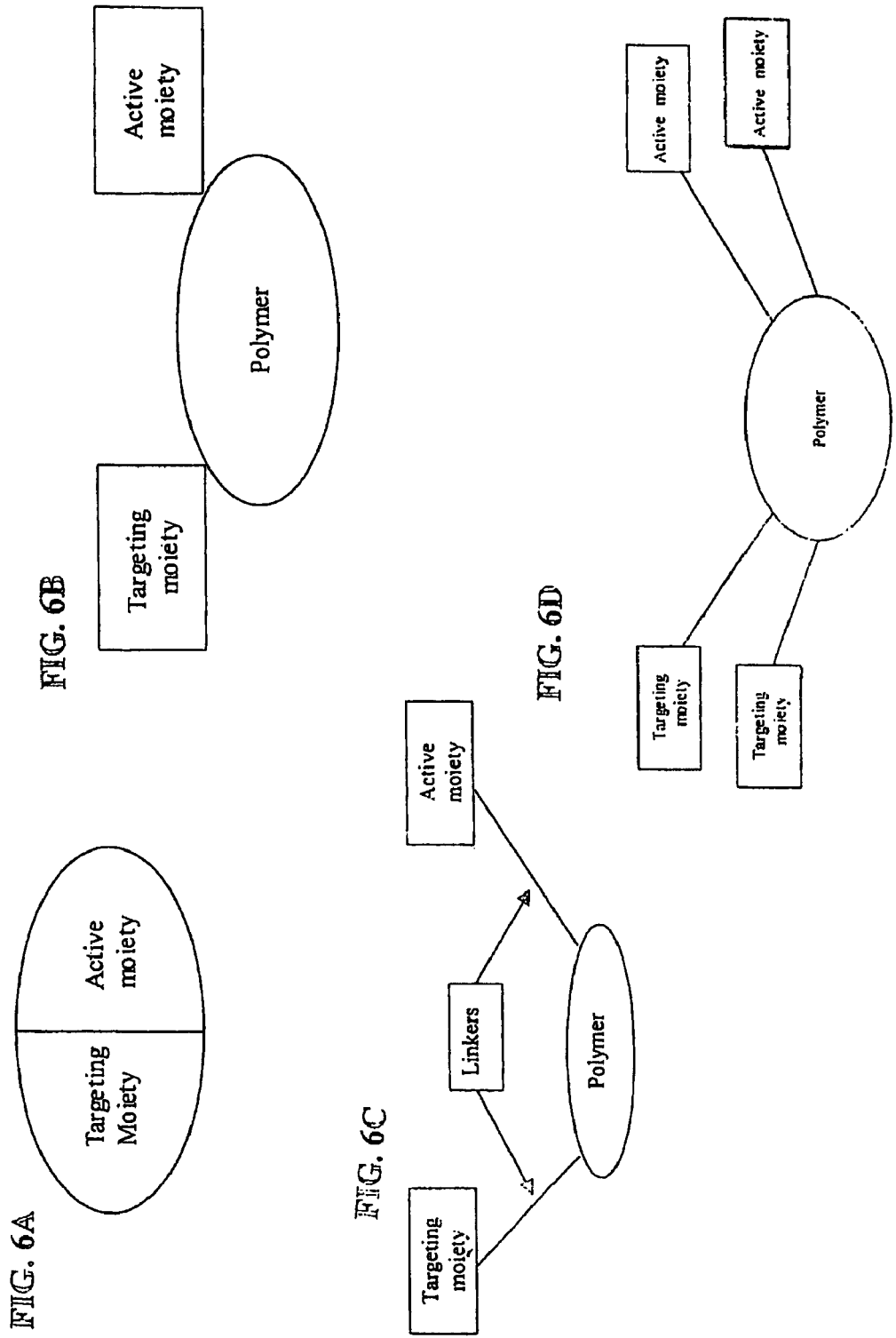
FIG. 6 is a schematic view of several embodiments of the reagent that acts upon the transfer surface to adhere it focally to the target, or focally change permeability of the transfer surface to the target.
Figure 7:
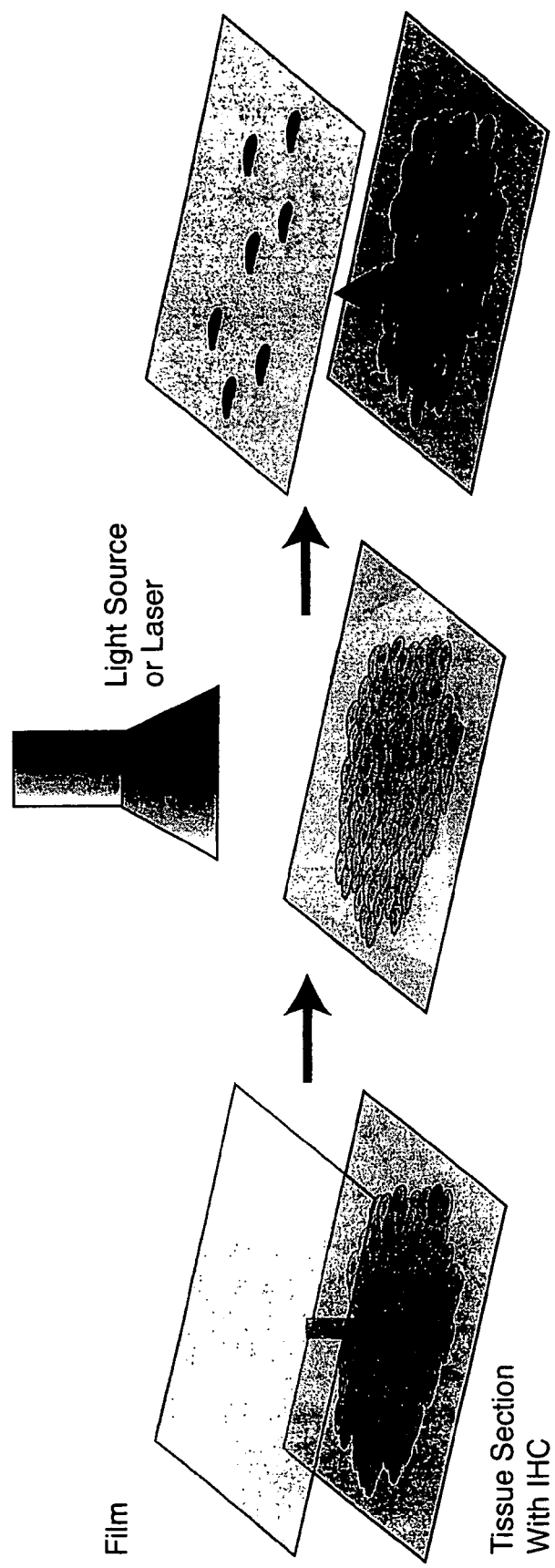
FIG. 7 is a schematic view of one embodiment of the method, in which the tissue section is stained with an immunohistochemical reagent, a transfer layer is placed on the stained tissue section, substantially the entire transfer layer is simultaneously irradiated with a single source of light, and the transfer layer is removed from the tissue section to remove stained target cells of interest.

Certain examples of the reagents include a targeting moiety and an activating moiety joined by a linker, although such a linker is not required. Many sorts of different chemical structures may constitute a linker (e.g., a peptide-to-peptide bond, a covalent bond between two protein domains, such as an amide, ester, or alkylamino linkages, or a single translated protein having two moieties "linked" by a series of residues). One non-limiting example of a linker is a synthetic sequence of amino acids. An example of a specifically contemplated complex linker (as illustrated in FIG. 6) includes a polymer molecule, which serves as a central structural substrate; and one or more simple linker components, which connect the polymer to the targeting and active moieties.

Other examples of linkers include a streptavidin linkage, a straight or branched chain aliphatic group, particularly an alkyl group, such as $C_1$-$C_{20}$, optionally containing within the chain double bonds, triple bonds, aryl groups or heteroatoms such as N, O or S. Substituents on a diradical moiety can include $C_1$-$C_6$ alkyl, aryl, ester, ether, amine, amide, or chloro groups.

Some linkers are complex, in that they are made of more than one component. An example of a complex linker is shown in the general schematic of FIGS. 6C and 6D. In one embodiment the complex linker includes a dextran polymer to increase solubility.

The dextran polymer is approximately 70-500 kDa in size, joined to one or more targeting moieties (such as goat anti-mouse IgG antibody), and one or more activating moiety (in this case an adherence activating molecule, such as a heat-generating enzyme) by covalent bonds created to simple linker molecules (such as bis(sulfosuccinimidyl)suberate ($BS^3$), sulfosuccinimidyl-4-(N-maleimidomethyl)cyclohexane-1-carboxylate (S-SMCC), N-succinimidyl S-acetylthioacetate (SATA), Dithiobis(succinimidylpropionate)(DSP), etc.). In some embodiments, further chemicals are used to catalyze formation of chemical linkages between the elements of the complex linker (e.g., a modifier S-acetylthioglycolic acid N-hydroxysuccinimide ester).

Complex linkers can be joined by streptavidin with biotin; these molecules can be attached to two protein or nucleic acid domains, and the interaction between the strept/avidin:biotin binding pair can serve to link the domains of a DCTM fusion molecule. Additional types of bond combinations that may serve to link molecules are amino with carboxyl to form amide linkages, carboxy with hydroxy to form ester linkages or amino with alkyl halides to form alkylamino linkages, thiols with thiols to form disulfides, thiols with maleimides, and alkylhalides to form thioethers, for instance. Hydroxyl, carboxyl, amino and other functionalities, where not present may be introduced by known methods. Examples of specific linkers can be found, for instance, in Hennecke et al. (*Protein Eng.* 11: 405-410, 1998); and U.S. Pat. Nos. 5,767,260 and 5,856,456.

Linkers may be repetitive or non-repetitive. One classical repetitive peptide linker used in the production of single chain Fvs (SCFvs) is the $(Gly_4Ser)_3$ (or $(GGGGS)_3$ or $(G_4S)_3$) linker. More recently, non-repetitive linkers have been produced, and methods for the random generation of such linkers are known (Hennecke et al., *Protein Eng.* 11:405-410, 1998). In addition, linkers may be chosen to have more or less secondary character (e.g., helical character, U.S. Pat. No. 5,637,481) depending on the conformation desired in the final fusion molecule. The more secondary character a linker possesses, the more constrained the structure of the final fusion molecule will be. Therefore, substantially flexible linkers that are substantially lacking in secondary structure allow flexion of the fusion molecule at the linker.

In general, the linker used is of a length and secondary character to hold the activating moiety within proximity of the target cell or cell structure after the targeting moiety has interacted with its target molecule. Examples of suitable lengths of the crosslinkers are approximately 25-100-Angstroms. For example, the linker spacer arm is 32 Angstroms long. In specific embodiments, a simple chemical linker is attached to a polymer through biochemical or other means, and a "modifier" is used to attach one or more copies of the targeting moiety and one or more copies of the activating moiety, to the polymer (FIG. 6D). In one example, the linker is the polymer poly(1-lysine hydrobromide) 40,000-60,000.

In some embodiments, the reagent is synthesized using peptide linkages to assemble the component moieties, for instance as described in U.S. Pat. No. 6,307,018. In such embodiments, peptide portions of the reagent are generated, then ligated together to form a native peptide linkage through intermediate steps. Alternatively, where the reagent can be synthesized as a single expressed nucleic acid using recombinant DNA techniques such as those provided in Sambrook et al. (In *Molecular Cloning: A Laboratory Manual*, Cold Spring Harbor, N.Y., 1989), and Ausubel et al. (In *Current Protocols in Molecular Biology*, Greene Publ. Assoc. and Wiley-Intersciences, 1992).

EXAMPLE 11

Selection and Preparation of Biological Sample

A variety of biological samples can be analyzed using the methods disclosed herein, such as biopsy material, tissue sections, cell culture preparations, cell smears and cytology preparations. Particular examples of such samples include cytology preparations or freshly ethanol-, methanol-, or acetone-fixed tissue sections.

In certain embodiments, target molecules (such as proteins, carbohydrates, etc.) are already exposed in the sample without any additional manipulation to enhance interaction of the target with the targeting moiety. However, it is sometimes useful to treat the biological sample, such as a tissue specimen, with a perforating buffer (such as saponin) or a solubilizer of a binding medium. Examples of solubilizers include cyanogen bromide solubilization of transferrin polypeptides and glycopolypeptides from formalin-fixed, paraffin wax-embedded tissue sections, (see Brooks et al., *Histochem J.* 30(8): 609-15, 1998); or de-waxing of ethanol-fixed, paraffin-embedded tissue sections in xylenes, followed by hydration and equilibration in Tris-buffered saline with Tween-20.

In some embodiments, such as those in which the targeting moiety interacts with cell surface molecules only, no permeabilizing treatment is necessary, though it optionally can be used. In other embodiments, pretreatment of a prepared cell or tissue sample is performed (e.g., exposure to proteinase K buffer, incubation with saponin detergent, polylysine, polyarginine, poly (lysine-arginine) or similar polypeptides, such as polycationic dendrimers) to enhance the ability of biomolecules (such as the targeting moiety) to interact with the sample (see Masuda et al., *Nucleic Acids Res.* 27(22): 4436-4443, 1999). The tissue may also be treated with agents to denature or otherwise inhibit Rnase or proteases. In some embodiments, samples are prepared using a fixative (e.g., methanol) that permeabilizes the sample, which can enhance the ability of an applied reagent to interact with the tissue sample. Such a treatment allows the reagent to penetrate below the surface of a tissue section.

For general preparation of frozen section biological samples, slides are prepared by placing 1% agarose on a standard histology slide and applying a cover slip. After a short period of time (for example about 5 minutes), the cover slip is removed, leaving a thin gel on the slide. A small frozen tissue section (for example about 25 microns thick) is placed on the agarose gel and optionally briefly stained with eosin. The sample may also undergo additional treatments to improve the specificity of the bonding between the targeted cells and the transfer substrate. For example, the support slide on which the tissue section is mounted can be made of a material that has an inherently lower affinity for the biological sample than the activated transfer substrate has for the biological sample. Alternatively, the slide can be pretreated with a monolayer of silicone oil or 3% aqueous glycerol solution to reduce the adhesion of the biological sample that is placed on the slide and increase the ease with which the transfer substrate transfers the tissue. However, more commonly, the support slide and transfer layer will be made of sufficiently different materials that the action of the activating moiety will alter only the transfer member and not the support slide. For example, the support slide may be made of glass and the transfer layer of a thermoplastic film, so that heating of the target will selectively adhere the target to the thermoplastic film but not the glass support. The melting temperature of the support slide and thermoplastic film are sufficiently different that the heat of the target only melts, fuses to or activates the thermoplastic film.

In another embodiment, the biological sample or transfer substrate is coated with silicone oil or a directly bonded silicone polymer, to decrease affinity between the transfer substrate and regions in the biological sample that do not contain the reagent. Activation of the reagent will cause focal melting of the transfer substrate to the targets, and will thus disrupt and dilute the surface monolayer of release agent only in the regions that undergo microtransfer. Therefore, the ability of the targeted cells or cellular components to undergo microtransfer is unaffected by the release agent, while the remaining portion of the biological sample will have a very low attraction to the transfer substrate as it is being removed from the biological sample.

In another embodiment, an adhesive layer such as poly-L-lysine is coated onto the slide prior to application of the biological sample. This adhesion strengthens the attachment of the biological sample to the slide, thereby reducing non-specific transfer when the transfer substrate is removed following activation of the reagent. Although such a treatment may make specific transfer less complete (for example by requiring greater bond strength of the transfer substrate with the underlying biological sample), the adhesive coating can also decrease the removal of non-targeted tissue from the biological sample.

In another embodiment, one surface of the biological sample is coated with a polymeric material that is placed against the transfer substrate. When the reagent in the targets is activated, the polymer forms a strong bond with the transfer substrate in areas containing the reagent. The polymeric material is sufficiently water-soluble to allow the biological sample to be retrieved for analysis by washing the sample to remove the polymer.

EXAMPLE 12

Application of Reagent to Biological Sample

The reagent is applied to the sample in a manner that it localizes to the target, because of the binding affinity of the targeting moiety for the target. In some embodiments, the reagent is applied by suspending the molecule in a buffer (e.g., 50 mM Tris-HCl, pH 7.5, 1% Triton X-100) and applying the buffer to the sample, for example by direct application to a tissue section as a spray or a layer of liquid that is coated on the sample. The reagent solution may optionally include an enzyme inhibitor, such as an RNase inhibitor, a DNase inhibitor, a protease inhibitor, and mixtures thereof. In some embodiments, the reagent is applied by automated means, for instance by an automated immunostainer such as would be used during an automated ELISA procedure (e.g., a Dako instrument, Dako Corporation, Carpenteria, Calif.).

In some embodiments, the samples are washed during application of the reagent solution, and/or after the reagent solution is applied. Washing is performed by applying a wash buffer to a sample on a slide, or by rapidly dipping a slide bearing the sample in and out of a wash solution, or washing by automated means, such as a robotic arm. This washing removes unbound reagent to lessen nonspecific adherence of the biological sample to the transfer substrate. Useful solutions for washing the tissue sample include, but are not limited to, phosphate-buffered saline (PBS), distilled water, diethylpyrocarbonate (DEPC) treated water, Tris-buffered saline (TBS), ethanol-water solutions, RNAsecure™ (to inactive RNAses) (Ambion, Austin, Tex.) and mixtures thereof. Wash solution may also include a surfactant, such as a nonionic detergent, for example Tween 20, 40, 60, 80, or 100.

In one example, histopathology slides are produced using traditional techniques (see e.g., Shin et al., *Lab. Invest.* 64(5): 693-702, 1991). Following fixation of tissue samples to the slides, the samples are subjected to automated enzyme-linked immunosorbant assay (ELISA)—like techniques (see Erdile et al., *J. Immunol. Methods,* 258(1-2): 47-53, 2001) to introduce the reagent into the tissue and allow binding of the targeting moiety (for example an antibody) to its target.

EXAMPLE 13

Application, Fusion and Removal of Transfer Substrate

Following the application and localization of the reagent to the targets, a transfer substrate is applied to the sample. The transfer substrate is optionally transparent to allow samples to be visualized, for instance with a microscope; however, transparency is not required. The transfer substrate may simply be placed on top of the biological sample (such as the tissue section) and compressed against it to assure that the substrate and sample are in good contact across their adjoining surfaces. Alternatively, the transfer substrate is fixed to the biological sample support by clips, guides, tape, standard adhesives, or similar convenient means The transfer substrate is characterized by its ability to be altered by the reagent in the target, to allow selective removal of the target from the sample. This alteration is accomplished, for example, by a physical or chemical change that is activated by the reagent. In those examples in which the change is an increase in temperature sufficient to adhere the sample to the substrate, the change is often a melting of a thermoplastic layer to adhere it to the targets in the sample. While wishing not to be bound by theory, it is believed that when a thermoplastic film is heated to near or at its melting point, the thermoplastic material liquifies to flow and conform to an adjacent surface (in this case, the target), forming a strong surface bond. This particular thermoplastic bond is believed to occur without actual chemical cross-linking to the tissue sample. However, other transfer substrates can form chemical bonds to the target upon activation of the substrate.

Adherence of the transfer substrate to the biological sample can also be enhanced by applying particles of thermoplastic polymer, in the form of a powder or as an unpolymerized solution, to coat the surface of the tissue sample on which the transfer substrate is placed. The particles of thermoplastic polymer can be applied, for example, in a drop or thin gel of suspended polymer molecules, or by dipping a tissue section fixed to a slide or other support into a liquid solution of the polymer.

Although the transfer layer and tissue support have been depicted as being on opposite surfaces of the tissue section, with the tissue section sandwiched between them, other arrangements are possible. For example, the transfer substrate and thermoplastic polymer may be applied directly to the support medium, and the tissue sample placed on top of the polymer. In one example of such an embodiment, the support medium may have two or more layers, with a strong under layer (for example of plastic or glass) and a thin thermoplastic substrate mounted on the support medium. The tissue sample is then applied directly to the polymer layer on the support medium, or directly to the thin thermoplastic layer. Activation of the reagent adheres the target to the thermoplastic layer, and the support surface and thermoplastic layer are then separated from each other (for example by peeling one away from the other) to selectively remove the target from the sample.

In embodiments in which thermoplastic particles are applied to the biological sample prior to application of the transfer substrate (or to the transfer substrate prior to application of the biological sample), the stimulus (such as a flash lamp pulse, laser pulse, addition of substrate for an activating moiety enzyme) causes the reagent to heat and transfer the heat by thermal diffusion to the thermoplastic particles that are in contact with those cells. As the stimulus is applied only briefly, the generated heat dissipates through the transfer substrate, thermoplastic particles, and biological sample rapidly (for example within a few milliseconds). The thermoplastic polymer will only melt if heated sufficiently (for example to 80° C. for ELVAX 510 ethylene vinyl acetate). Thus, only the particles in contact with intensely stained cells (cells containing a threshold level of reagent) will melt and fuse to the target. The remaining particles will not be heated sufficiently to melt and consequently will not adhere adjacent structures.

To increase the volume of thermoplastic polymer melted for a given stain level (OD), more flash lamp energy may be applied. Providing a single pulse of greater energy may be adequate to locally melt sufficient thermoplastic polymer to cause the adherence of cells containing a sufficient density of reagent to the transfer substrate in some instances. However multiple pulses, such as a series of flash lamp pulses of lower-intensity, can help reduce lateral enlargement of adherence that may result from application of a single strong stimulus. Each stimulus in the series is applied in an intensity sufficient only to cause adherence to target cells containing the reagent, thereby substantially avoiding adherence of non-stained cells to transfer substrate. Subsequent pulses improve the strength of the adherence by allowing melted thermoplastic polymer to expand and flow into/onto the targeted cells, which also allows the thermoplastic polymer to adhere more strongly to the transfer substrate.

EXAMPLE 14

Analysis of Adhered Components

Following removal of the target from the biological sample, the target may be subjected to further analysis. For example, after a thermoplastic transfer layer is focally adhered to the targets and then removed from the sample, the transfer layer is separated from the sample and the adhered components are reserved for subsequent analysis. In one example, the transfer substrate itself is introduced directly into a tube that contains buffer. Alternatively, the targets may be flash-frozen on the transfer substrate, or the targets may be fixed to a separate stable medium (such as a glass slide). In other embodiments, the targets are physically cut from the transfer substrate, focally dissolved from the transfer substrate, or excised with a hot wire knife that (which is self-sterilizing to eliminate contamination between specimens).

The biological material in the targets, such as cells or cellular components, are amenable to methods of analysis known in the art, such as those provided in Sambrook et al. (In *Molecular Cloning: A Laboratory Manual*, Cold Spring Harbor, N.Y., 1989), and Ausubel et al. (In *Current Protocols in Molecular Biology*, Greene Publ. Assoc. and Wiley-Intersciences, 1992). Specific methods of analysis of the isolated components include resolution of proteins through electrophoresis (e.g., SDS-PAGE), followed by visualization using an appropriate method (e.g., blot staining with Ponceau S, autoradiography, etc.), and those in which the isolated components are sequenced or amplified, for instance using the polymerase chain reaction, and subsequently visualized on a gel, or in an array, etc.

To analyze enzyme activity of cells procured by the method, the procured cells can be placed in an appropriate buffer depending on the enzyme of interest. The enzyme levels can be measured by several methods including zymography and the use of specific fluorometric substrates to determine the precise levels of enzyme expression in a specific cell population.

Another type of assay that can be used to analyze the extracted components is two-dimensional polyacrylamide gel electrophoresis (2D PAGE). By running proteins extracted from cells of a control sample and proteins extracted from cells of an experimental sample (such as a tumor sample) and comparing the blots, differential protein expression can be seen. In particular, by scanning the stained gels into a computer, and using image comparison software, the location of proteins that are present in one cell type and absent in the other can be determined. Furthermore, these altered proteins can be isolated from the gel where they are present, and mass spectroscopy MS-MS sequencing can be used to identify the protein, if the sequence exists in a database. In this way, the protein differences between control and experimental cells can be more fully understood. Additionally, proteins of interest isolated from a 2-D gel may be used in binding studies, where the protein is functionally tested for an alteration in the ability to bind with a putative or known ligand. Finally, this comparative analysis can be performed on samples from various stages of progression of a disease (i.e., isolated stages of a tumor), where the different stages exhibit sufficient differences to allow separate isolation of populations using the methods disclosed herein.

For messenger RNA analysis, isolated cells can be placed on agarose and treated with agents to denature RNase if necessary. The procured cells are then used immediately, or frozen in liquid nitrogen for storage at −70° C. for several months. The mRNA can be extracted using an oligo dT column (Micro-Fast track mRNA Isolation Kit, Invetrogen Co.). Recovered mRNA can alternatively be amplified and investigated using polymerase chain reaction (PCR) technology, such as, for example, by RT-PCR as known to those skilled in the art.

To analyze DNA from cells isolated by the present method, the isolated cells are extracted (e.g., placed in a single step extraction buffer solution of 50 mM Tris, pH 8.5, 1 mM EDTA, 0.5% Tween 20, and 0.2 mg/ml proteinase K, incubated for four hours at about 37° C., followed by ten minutes incubation at about 95° C.). Recovered DNA can also be amplified and analyzed using PCR technology in combination with analysis techniques, such as blotting, sequencing, etc., known in the art. If native DNA is required for DNA fingerprinting analysis, the proteinase K can be added after DNase in the fingerprinting protocol. For DNA analysis of paraffin embedded tissue, the isolated cells are extracted, (e.g., placed in a single step extraction buffer solution of 50 mM Tris, pH 8.5, 1 mM EDTA, 0.5% Tween 20, and 0.2 mg/ml proteinase K), and incubated (e.g., depending on sample size, from two to twenty-four hours at about 37° C., followed by a ten minute incubation at about 95° C.).

If the extracted cells contain, or are suspected to contain, proteins or polypeptides of interest, the extracted sample can be subjected to enzyme zymography, for example using one or more labeled substrates, immunoassays utilizing, for example, labeled antibodies or functional fragments thereof, biochemical assays, and the like.

In other embodiments, the transfer substrate can be treated with suitable reagents to analyze the constituents of the transferred material. This can be accomplished by submerging the transfer substrate, to which the procured cellular components are adhered, in a suitable reagent solution. Alternatively, one or more of the procured cellular component regions is removed from the transfer substrate, or portions of the transfer substrate to which the procured cellular components are adhered can be cut from the transfer substrate. These separated sections of the transfer substrate are then analyzed separately.

EXAMPLE 15

Use of an Antibody-Enzyme Reagent

In one particular example, an antibody-enzyme reagent is provided and applied to a fixed sample (such as a tissue section fixed on a glass slide). The activity of the antibody (targeting moiety) is used to bind the reagent to target cells in the sample. The activating moiety consists of an enzyme that cleaves exogenously supplied alkaline phosphatase substrate [e.g., 2-5'-chloro-2-phosphoryloxyphenyl)-6-chloro-4(3H)-quinazolinone] to create an extremely fine precipitate that remains well localized to the site of enzymatic activity (see Paragas et al., *J. Microsc.* 206(Pt 2):106-119, 2002). Thus, the enzyme activity provides localized deposit of absorptive material only within target regions. In such embodiments, the enzyme activity is continued until the local absorption at sites of high DCTM molecule localization is sufficient (for example absorbing approximately 20-90% of the incident light). Following deposit of stain, a thermoplastic film is placed over the tissue section and placed firmly against the surface of the tissue section to assure adequate thermal contact between the thermoplastic film and tissue section. The tissue section is then exposed to a brief light flash (such as a 200 Joule flash lamp or laser diode pulse), which causes the stained tissue to locally heat (for example up to 100° C.) in target regions of the tissue section that contain the stain. Wherever the applied transfer substrate is in sufficient thermal contact with tissue in which the contrast of absorptive material deposit to areas containing no deposit reaches a sufficient threshold (for example at least about 30%), differential focal adherence of the thermoplastic film to the target regions will occur.

In an alternative example, a low melting point thermoplastic powder is used as (rather than in conjunction with) a transfer substrate. An example of a thermoplastic powder suitable for such purposes is Dupont ELVAX 510 gel or powder, which can be made into a thin film that melts and expands (for example with an expansion of about 25% at 80° C.).

EXAMPLE 16

Specific Examples of Research and Diagnostic Applications

Use of the present methods to separate or isolate targets from the biological specimen is useful in diagnosing disease, using a variety of medical specimens, such as tissue sections, cells in culture, cytology preps, or cells in vivo.

A. Detection of Injured Tissue Using Fluorescing DCTM Molecules

Fluorescing reagents are useful in diagnosing injured tissue. For example, in injured kidney tissue, expression of the Tamm-Horsfall protein is known to decrease following renal ischemia, but detection of ischemic thick ascending limbs with fluorescent antibodies against the Tamm-Horsfall protein is difficult. However, the amount of Na—K-2Cl co-transporter does not decrease following ischemia (see Fernandez-Llama et al., J. Am. Soc. Mephrol., 10: 1658-1668, 1999 and Kwon et al., Am. J. Physiol. Renal Physiol., 278: F925-F939, 2000). Thus, immunoreagents with fluorescent antibodies specific for the co-transporter protein are useful for identifying ischemic thick ascending limbs.

In a specific embodiment, an immunoreagent is made that has an antibody directed to the Na—K-2Cl co-transporter protein, and an activating moiety that activates adherence of cells containing the protein to the transfer substrate. Following targeting and microtransfer, the targeted proteins are transferred into a tube and analyzed (e.g., sequenced or further amplified using polymerase chain reaction and subsequent visualization on a gel).

B. Screening for Diseased Cells

Microtransfer of targeted biomolecules allows for more efficient and specific analysis of cell populations within heterogenous tissue samples than by conventional techniques. The microtransfer technique of the present disclosure may be used in combination with a number of different technologies that allow for analysis of enzymes, mRNA and DNA from pure populations or subpopulations of particular cell types.

For example, DNA can be microtransferred, using the methods of the present disclosure, from populations of cells specifically obtained from normal epithelium, pre-malignant lesions, and invasive cancer in a single patient's tissue section(s). Differential gene expression libraries can then be generated by standard RT-PCR, using methods known to those of ordinary skill in the art. Such expression libraries represent cellular stages of cancer progression, and can be used to screen for cancer diagnostic and prognostic markers. This approach can identify markers of disease by, for example, profiling protease distribution during tumor invasion, identifying the location of protease expression in tumor and/or stromal cell populations as an indicator of tumor aggressiveness, and providing the ability to monitor the effectiveness of anti-protease therapeutic agents in inhibiting protease activity at the tumor-stromal interface. In addition, combination of targeted microdissection methods with PCR, RT-PCR, differential display and SSCP is capable of identifying genetic alterations in specific subpopulations of tumor or stromal cell that would not be evident in heterogeneous human tumor samples.

Microdissection is also useful in routine diagnosis of tumors, such as the identification of pre-malignant lesions of all types of cancer, genetic analysis of infectious diseases, gene therapy, tissue transformation, and gene localization and analysis of transgenic animals. Additional applications include analysis of the genotype, cellular products, or infectious organisms of rare populations such as monocytes infected with drug resistant organisms, Reed-Stemberg cells of Hodgkins disease, Kaposi's sarcoma cells, stem cells, and vessel cells. Moreover, genetic analysis or identification of microorganisms infecting microscopically visualized cells in tissues, lymph nodes or inflammatory areas can also be achieved with high precision using DCTM molecules and methods.

EXAMPLE 17

Automated Analysis

The ability of the targets to "self-identify" once they have been exposed to the reagent, and then select themselves for adherence to (or movement through) the transfer layer, makes this method ideally suited to automation. For example, hundreds or thousands of tissue specimens can be exposed to an immunoreagent that carries a fluorophore to localize the reagent in the targets. The tissue specimen is then robotically covered with a light-transmitting thermoplastic transfer layer. Each such unit is next illuminated with multiple flash lamp pulses at a wavelength that excites the fluorophore, which induces the fluorophore to emit heat and melt the thermoplastic layer to adhere the target to the thermoplastic layer. The transfer layer can then be robotically removed from each unit, and introduced into an analysis tube for further automatic evaluation. Such automation increases the efficiency of producing and analyzing samples, reduces operator error, increases consistency of results.

In one automated embodiment, multiple tissue section slides are fixed to individual supporting media (e.g., glass slides), and the samples are subjected to automated ELISA (e.g., Trinity Biotech ELISA Processor, Trinity Biotech PLC, Co., Wicklow, Ireland) or ELISA-like procedures using a DCTM molecule, for instance where the DCTM molecule is an antibody-enzyme fusion molecule. After processing of the ELISA using an automated immunostainer (e.g., a Dako instrument, Dako Corporation, Carpenteria, Calif.), thermoplastic polymer and a transfer substrate are applied to the top of the supporting media (e.g., by application of a suspension of polymer molecules) such that the transfer substrate is in good thermal contact with the sample. Subsequently, the activating moiety is activated to cause the immunostained cells to adhere to the transfer substrate layer. The components of interest then can be automatically separated from the support medium environment through removal of the transfer substrate, and the components of interest placed into individual containers for subsequent analysis (which may also be done by automated methods). In examples of such embodiments, each slide contains several hundred thousand to a million or more cells of interest, and the automated process is completed in a few hours, as opposed to the greater than one week of operator time necessary using traditional laser capture microdissection techniques.

EXAMPLE 18

Genomic and Proteomic Applications

Using the methods disclosed herein, high throughput functional genomics and proteomics can be brought down to the level of individual cells in a tissue. Following separation of targets from the biological sample, the analysis of protein, mRNA, and other component levels from isolated specific cells and tissue structures helps determine whether and to what extent genes are operative in normal as compared to diseased cells. Isolation of specific cells using these methods makes it possible to detect, for example, somatic mutations in cellular DNA that result in malignancy. The methods can be used to follow changes in gene expression that accompany cell maturation, tumorigenesis, and cell apoptosis (by targeting the reagent to cells having these characteristics). Furthermore, the identification and isolation of specific protein products specifically produced by diseased cells provides information that can be used to develop new diagnostic methods to scan for the presence of such proteins. Each of these areas can be advanced by the methods disclosed herein, which enable selective isolation of specific cells or cellular components (e.g., DNA, RNA, proteins, and mRNA) from target tissue samples having target characteristics (such as atypia, viral infection, or aggressive infiltrative tumor cells).

Subjecting purified populations of cells to high-throughput genomic or proteomic analysis can also be used to correlate disease prognosis or therapeutic outcome with molecular characteristics, such as structural changes in genes or proteins, copy number or expression alterations of genes. Genomic and proteomic analysis can also identify novel targets for gene prevention, early diagnosis, disease classification, or prognosis; and to identify therapeutic agents.

Examples of high-throughput technologies that can be used for these and other purposes include cDNA and genomic sequencing, serial analysis of gene expression (SAGE), representational difference analysis (RDA), differential display and related PCR-based technologies, hybridization-based sequencing, subtractive cDNA or genomic hybridizations, cDNA arrays, Comparative Genomic Hybridization (CGH) arrays, electrophoretic, mass spectrometric, or other separation and identification methods (including SELDI fingerprinting) for DNA or proteins, yeast two-hybrid technology or related techniques of molecular biology.

A particular example of a high throughput proteomic technique that may be combined with the target activated transfer of the present disclosure is SELDI protein fingerprinting. SELDI analysis of proteins from samples obtained by target activated transfer may be used, for example, to assess changes in protein expression occurring during tumor progression following analysis. SELDI analysis of pure populations of cells and tissue structures provides a more complete picture of cell level proteomics that includes proteins with cell surface receptors, for instance. Such information will aid in the elucidation of the fundamental mechanisms underlying disease and identification of markers that may be utilized for diagnostic purposes. Such analyses are not however restricted to a particular disease state and may also be utilized to elucidate mechanisms of tissue damage and repair in response to injury, chemical, physical, or otherwise.

Purified cell and tissue structure samples obtained by target activated transfer may also be used in combination with array techniques, and can provide information about the frequency of a multitude of genetic alterations or gene expression patterns (including normal gene expression patterns) in a variety of tissue types (such as different types or grades of tumors), and in tissue of a particular histological type (such as a tumor of a specific type, such as intraductal breast cancer), as well as the tissue distribution of molecular markers tested.

Differential gene expression can be analyzed by detecting different levels of proteins or RNA using semi-quantitative RT-PCR on the substantially pure cell populations obtained by the targeted transfer techniques described herein. Once the differential expression is determined using this approach, the different levels of expression can be used for diagnostic or therapeutic purposes. For example, overexpression or underexpression of particular proteins can be associated with particularly benign or malignant tumors, which provides prognostic information about the likely clinical course of a tumor. This information in turn helps determine whether particularly aggressive anti-tumor chemotherapy must be undertaken to obtain a greater likelihood of response or remission. Similarly, information about differential protein expression in particular types of disease (such as tumors of a particular type) can be used to target treatment. Hence if up-regulation of a protein is found in a particular type of tumor cell, therapies aimed at disruption of that up-regulation can be administered.

EXAMPLE 19

Kits

Transfer of targets from biological samples can be performed with a kit that includes a transfer surface and a reagent. The transfer surface may be, for example, a heat-responsive thermoplastic film. The reagent may be any agent that selectively binds to the target of interest and is capable of producing a change in the transfer surface, for example to focally adhere the target to the transfer surface, or to focally increase permeability of the transfer surface to the target. In specific embodiments, the reagent includes the targeting moiety to specifically bind to the target, and the activating moiety that is capable of selectively changing the transfer surface. Any of the examples of the reagent and transfer surface that have been described above are suitable examples of materials that are included in the kit. In those examples in which the activating moiety is activated by exposure to an activating agent, such as light and/or a catalyst substrate, the activating agent may also be included in the kit.

In one particular example in which the reagent is an immunoreagent that carries a fluorophore and a catalyst (such as horseradish peroxidase), the kit would include the immunoreagent and the substrate for the reagent (such as diaminobenzene and a metal). Optionally, the kit could also include a light source (such as a flash lamp) that emits light of a wavelength that would activate the fluorophore of the immunoreagent.

Kits can also be contained in a carrier, such as a box, a bag, or plastic carton. In one embodiment the carrier contains one or more containers, for instance vials, tubes, and the like, that include at least one reagent that specifically binds to the target, and at least one transfer substrate.

Instructions can be provided to detail the use of the components of the kit, such as written instructions, video presentations, or instructions in a format that can be opened on a computer (e.g., a diskette or CD-ROM disk). These instructions indicate, for example, how to use the reagent and transfer film to transfer the target from the biological specimen.

Kits may additionally include one components of the reagents that can be used for making the reagents. For instance, such components may include targeting or activating moieties, linkers, buffers, and/or components for recombinant synthesis of the reagent. These reagents may be provided in bulk, where each container of reagent is large enough for use in several synthesis procedures. Alternatively, the reagents can be provided in pre-measured aliquots, which can be tailored to the type of reagent synthesized.

The kits may contain a standardized reagent, in which the targeting moiety is a secondary antibody that has affinity for a number of different primary antibodies (for instance, an anti-IgG antibody reactive to IgG produced from a specific species). Using such kits, the user can select a primary antibody (that may or may not be in the kit) based upon the desired target population, and the standardized secondary antibody is used to detect the primary antibody in the biological sample.

Those of ordinary skill in the art know the amount of targeting moiety that is appropriate for use in a single detection reaction based on uses known in the art (such as the existing use of fluorescent immunoreagents). General guidelines may for instance be found for the use of antibodies, DNA probes, and receptor binding reactions in Innis et al. (*PCR Protocols, A Guide to Methods and Applications*, Academic Press, Inc., San Diego, Calif., 1990), Sambrook et al. (In *Molecular Cloning: A Laboratory Manual*, Cold Spring Harbor, N.Y., 1989), and/or Ausubel et al. (In *Current Protocols in Molecular Biology*, Greene Publ. Assoc. and Wiley-Intersciences, 1992).

Kits may additionally include one or more buffers for use with the target activated transfer methods. For instance, such buffers may include a low stringency, a high stringency wash, and/or a stripping solution for reagents in which the targeting moiety is a nucleic acid probe. These buffers may be provided in bulk, where each container of buffer is large enough to hold sufficient buffer for several washing or stripping procedures. Alternatively, the buffers can be provided in pre-measured aliquots, which can be tailored to the size and style of tissue targeting substance included in the kit.

Kits may also include one or more substrates that activate the activating moiety, such as substrate for an enzymatic activating moiety, as well as various thermoplastic polymers (such as thermoplastic particles or liquid), transfer substrates, or general components useful in the analysis, such as slides, coverslips, and tubes. Furthermore, kits may include materials that are useful in the analysis of targets selectively removed from the sample.

EXAMPLE 20

Devices for Target Activated Transfer

Devices for performing target activated transfer from a tissue sample are also disclosed herein. The devices include a mounting surface for mounting a tissue sample, and a light source positioned to irradiate the mounting surface with light energy that activates the reagent to selectively adhere targeted cellular material to a transfer surface. In some example, the light source is an immobile single light source that irradiates substantially the entire mounting surface in a single flash. Alternatively, the light source is a mobile light source that scans across the mounting surface. For example, when the light source illuminates less than the entire mounting surface, the mounting surface is movable to increase an area of the mounting surface that is illuminated by the light source. The mounting surface may be movable in a predetermined pattern to illuminate substantially the entire tissue sample mounted on the mounting surface. For example, a platform on which the mounting surface is located can move in a pattern that brings a light emitting diode into contact with substantially the entire portion of the mounting surface on which the tissue sample is mounted.

In operation, the tissue sample is mounted on the mounting surface (typically a glass microscope slide), and the tissue sample is stained with the reagent that localizes specifically at the targeted cellular material (e.g., standard immunohistochemical staining: typically a cell or organelle specific absorptive stain such as an enzyme-linked antibody which targets specific antigens within the tissue targets, a second step follows in which the specifically localized enzyme acts on an specific substrate added to the bathing solution in order to form an absorptive precipitate locally within the tissue where the antigen targets are present). The stained tissue sample is covered with a transfer surface to which the targeted cellular material adheres after the light source irradiates the tissue sample on the mounting surface.

Figure 13:
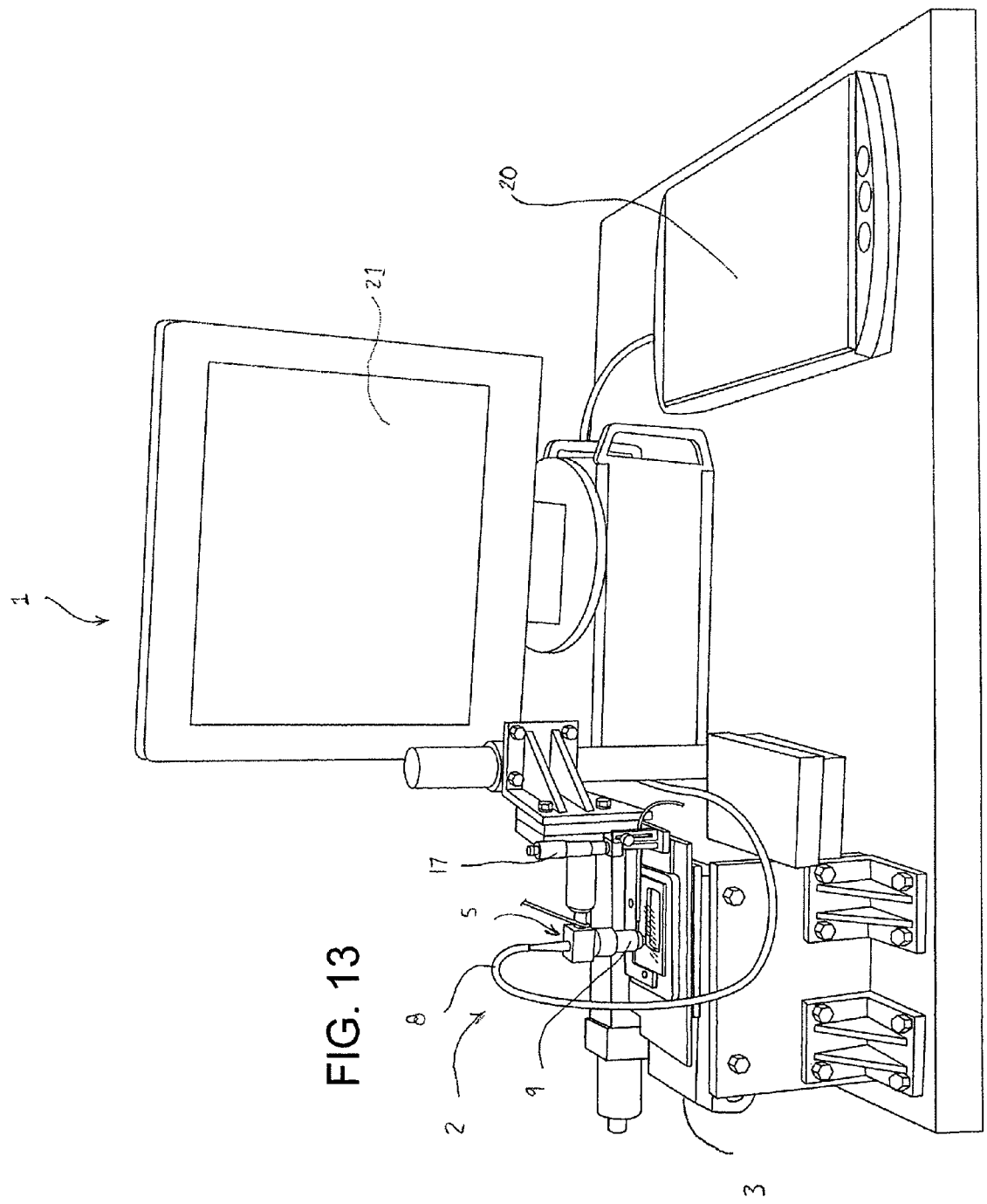
FIG. 13 is a perspective view of an example of an automated system for performing target activated transfer.
Figure 14:
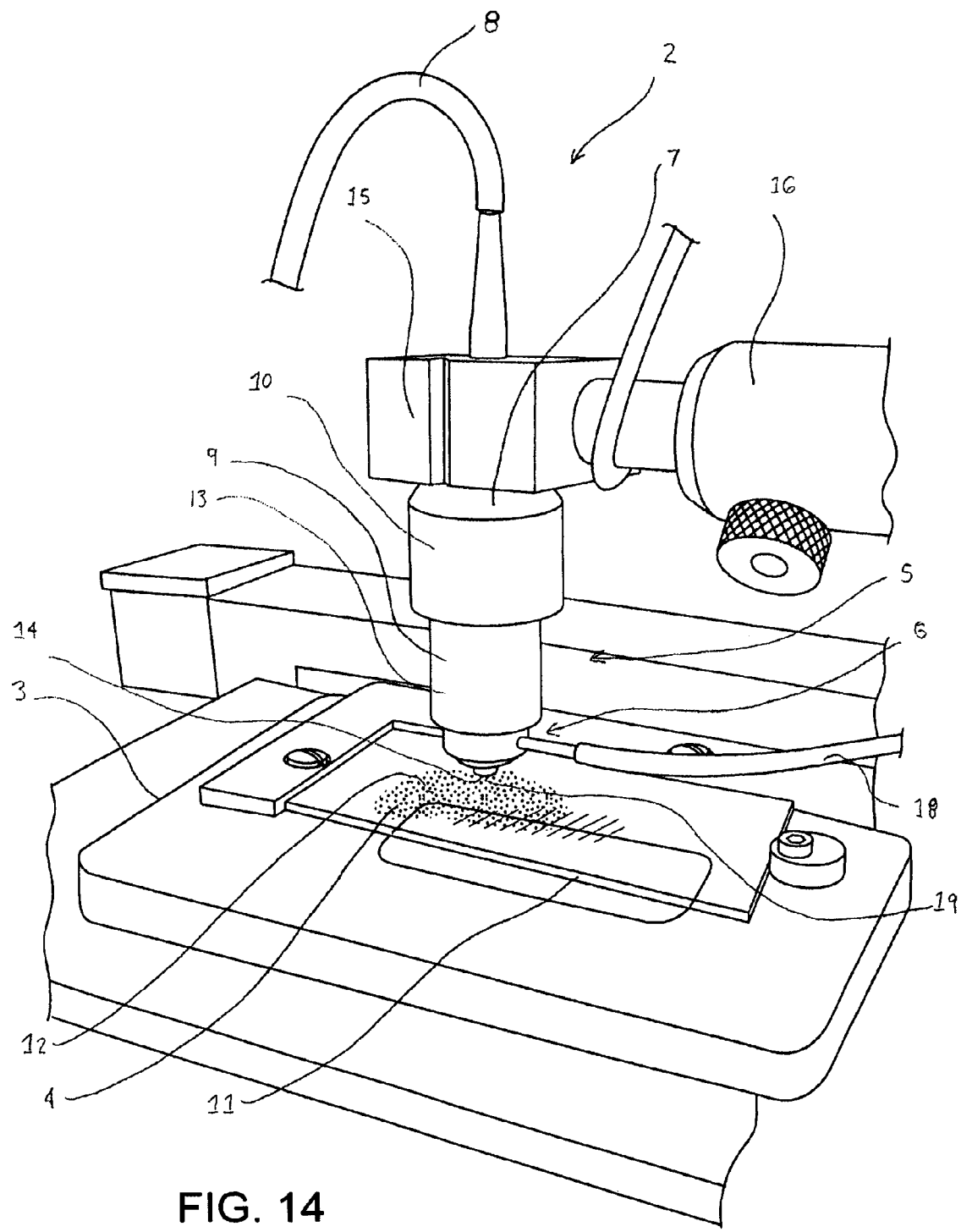
FIG. 14 is a perspective view a tissue transfer station that includes an irradiating member and an x-y translating stage.

An example of a target activated transfer system 1 is shown in FIG. 13 and an example of a tissue transfer station 2 is shown in FIG. 14. Although the automated scanner, controller, monitor and tissue transfer station are described in combination, the disclosure includes any of these sub-units in isolation, or in combination with any other sub-units.

The target activated transfer system 1 utilizes light energy (e.g., a scanned laser beam) absorbed by surface stains (e.g., standard absorptive immunostains using a DAB precipitate or standard absorptive histological stains or highly localized silver-enhanced immunogold labeling of organelles) in tissue sections to melt thin (~1 micron) layers of an overlying flexible thermoplastic film which due to applied air pressure (by, for example, an air-bearing) is forced onto the tissue. The air-bearing both insures sufficient and reproducible physical contact and thermal conduction between the locally heated tissue to allow the surface of the thermoplastic film to be efficiently melted in a short enough time to prevent significant heat loss and lateral melting of the thermoplastic film beyond the locations that are stained. Without intimate physical contact, thermoplastic film heating and melting would not occur. In addition, the air-bearing provides a self-regulating system that can adjust to irregularities in the surface profile to topology of the tissue example as explained below in more detail. The air-bearing can also create a constant local pressure to reliably force the locally melted thermoplastic polymer into the tissue section.

The target activated transfer system 1 includes a tissue transfer station 2. The tissue transfer station includes an x-y translating stage 3 to translate and scan a tissue section 4 via an irradiating assembly 5. The x-y translating stage 3 may be a high speed x-y scanner that can move in the x and/or y direction at programmable speeds, for example, from about 10 to about 80 mm/sec over a fixed pattern such as surface covering raster scan. The irradiating assembly 5 has a proximal end 6 and a distal end 7, and includes a fiber optic cable 8 that is optically coupled to the distal end 7 of the irradiating assembly 5. The fiber optic cable 8 is also optically coupled to a laser diode (not shown). In one example, two laser diodes can be interchanged to generate either infrared light of 830 nm wavelength or green light at 532 nm allowing for selection of laser wavelength to be matched to different colored stains.

The tissue sample 4 is mounted onto a mounting surface 11 (e.g., a slide). The tissue sample 4 includes an outer surface 12 that faces the proximal end 6 of the irradiating assembly 5. A transfer substrate (e.g., a thermoplastic film) (see element 16 in FIG. 1A) is disposed between the outer surface 12 of the tissue sample and the proximal end 6 of the irradiating assembly 5. The film includes an outer planar surface layer that faces the proximal end 6 of the irradiating assembly 5, and an opposing planar contact surface layer (see surface 14 in FIG. 1A) that faces the outer surface 12 of the tissue sample. This system has been designed to use commercially available tapes such as 3M ScotchPak tapes (a thermoplastic 25 µm EVA layer on a thinner 6 µm polyethylene terephthalate backing) used widely in the food processing industry and completely bio-compatible but insoluble in standard molecular extraction buffers. Such tapes include a strong temperature insensitive layer and a temperature sensitive thermoplastic adhesive layer.

The irradiating assembly 5 includes an optical assembly 9 that is received within a cylindrical sleeve 10. The cylindrical sleeve 10 includes a cylindrical bore within which the optical assembly 9 is slidably journaled so as to be moveable along the longitudal axis of the irradiating assembly 5 (i.e., in the z-direction normal to the plane formed by the outer planar surface of the transfer substrate). For example, the optical assembly 9 may be slip-fit within the cylindrical bore of the cylindrical sleeve 10 and the contact surfaces between the optical assembly 9 and the cylidrical bore may be lubricated to ease z-direction translation of the optical assembly 9. The optical assembly 9 may include two paired lenses that act as a telescope to reimage the uniform laser beam output from the fiber optic cable 8 onto the tissue surface. The optical assembly 9 may be any optical assembly that can precisely reimage a laser diode-generated laser beam that is propagated through a fiber optic cable. A suitable optical assembly 9, for example, is commercially available from Thor Labs. In certain examples, the optical assembly 9 includes a cylindrical housing 13 for two concentric lenses that collimate and refocus the laser beam, and in aggregate weigh an appropriate amount to determine the air-bearing contact force on the tissue/film interface (~4 g/mm$^2$).

The irradiating assembly 5 also includes a nozzle 14 that is a tapered cone that includes an aperture at its proximal end 6. The laser beam from the fiber optic cable 8 exits the irradiating assembly 5 via the aperture in the nozzle 14. In other words, the fiber optic cable 8 in the irradiating assembly 5 emits a laser beam that is directed towards, and illuminates, the tissue sample 4. The aperture in the nozzle 14 may range in diameter size from about 1 mm to about 10 mm, with 3 mm being especially suitable for an assembly weighing 30 g.

The cylindrical sleeve 10 is affixed to a holding block 15 that rigidly holds the cylindrical sleeve 10 in place relative to the x-y translating stage 3. The holding block 15 is supported by a support arm 16 that is mechanically coupled to the x-y translating stage 3 and a z-direction adjustor 17. The z-direction adjustor 17 can move the holding block 15 in the z-direction, if necessary.

Means for applying air pressure to the outer planar surface of the film are provided. The air pressure can be delivered by any suitable arrangement. In the example shown in FIGS. 13 and 14, an air-jet is provided within the irradiating assembly 5 that is coaxial with the laser beam. The coaxial air jet is coupled to a source of pressurized air (not shown) via an air line 18. The air line 18 is coupled to the irradiating assembly 5 via an orifice axially located below the position of the second lens in the optical assembly 9. The air from the air-jet exits from the proximal end 6 of the irradiating assembly 5 via the aperture defined in the nozzle 14 so that the forced air can be directed against the outer surface of the film. The air directed against the film serves at least three purposes.

As mentioned above, the air provides a substantially constant force against the film. The constant force allows the thin (e.g., about 40 to about 120 µm), flexible film to conform to the surface topology of the tissue sample. Moreover, due to the flexibility of the film and the forcing pressure acting on it as the lower thermoplastic surface locally melts where it contacts specifically stained regions, the molten film flows into and can form a bond with the full thickness of the relatively thin tissue sample. The fact that the film is initially in precise contact with the tissue surface and moves into the tissue in tiny increments (~1 µm) in proportion to the stain density and absorbed energy means that the precision and reproducibility of the tissue transfer increases dramatically over existing thermoplastic microbonding as in laser capture microdissection.

Second, the flow of the air between the surface of the nozzle 14 and the moving outer surface of the film creates an air-bearing that supports the slidable optical assembly 9 off of the outer surface of the film. In other words, the air-bearing creates a gap 19 between the nozzle 14 and the outer surface of the film. In certain examples, the gap 19 will be reliably maintained at about 1 to about 2 µm. The upward force exerted by the air flowing through the air-bearing gap 19 cushions the slidable optical assembly so that it can "float" on the air-bearing as it moves in the z-direction within the fixed sleeve 10. The air-bearing also self-regulates the system by maintaining a substantially constant force exerted against the film in the event of surface topology irregularities and/or changes in the air pressure and/or polymer melting and advancement into the porous tissue section. For example, if the air pressure in the air flowing through the air-jet increases the slidable optical assembly 9 will slide farther towards the outer surface of the film so as to maintain a sufficient upward force to support the weight of the optical assembly 9. The weight of the optical assembly, of course, is constant. Consequently, the downward force exerted against the outer surface of the film will also remain substantially constant.

Third, the force exerted by the air-bearing against the film can assist in maintaining the position of the film in registration with the position of the tissue sample as the tissue slide 11 moves via the x-y translating stage 3.

Although the system has been described above in terms of an air-bearing, air or any relatively inert gas such as nitrogen can be equivalently used to provide sufficient local pressure on the flexible polymer film via a gas-bearing. The flow rate in an air bearing may be sufficiently low that a tank of pressurized gas could be used as well as an air pump creating a constant pressure.

A pressurized fluid such as water could also be used to apply the pressure against the transfer film since the film in generally impermeable and insoluble to a variety of liquids. The use of pressurized liquid would require a sealed reservoir for the fluid (liquid or gas) with the film being a lower flexible wall fo this reservoir. The air-bearing system shown in FIG. 13 creates a local constant force without a closed system. In systems such as a whole field irradiation by a flash lamp it would be necessary to apply a uniform pressure over the entire tissue sample which may require the film to be the lower surface of a closed pressurized reservoir. The air-bearing is, on the other hand, a local constant pressure system particularly suited to a scanning system in which only a local region is irradiated at a given time.

There are also other possible embodiments for the tissue transfer system. For example, rather than a circular beam scanning the tissue, it is possible to use a cylindrical lens to create a slit beam as wide as the whole tissue sample so that a single line scan covers the entire tissue. In this case the air-pressure jet could be formed to correspond to this slit (note the air-bearing implies small air flow between the orifice (here a slit) and the surrounding planar surface that forms a thin gap with the tape surface). A flash lamp can be used to irradiate the entire tissue slide simultaneously thereby avoiding the requirement for any mechanical scanning (i.e., a very simple system). In such a case, a large constant pressure reservoir acting on the entire surface of the film (which would be the lower wall of the chamber) would be as effective. Alternatively, an appropriate differential force could be applied across the tape by a negative pressure (vacuum) applied to the tissue and lower surface of the tape. This is a common practice in vacuum forming for wrapping of commercial objects in a polymer film. In this case the desiccated tissue is intrinsically sufficiently porous but the substrate on which the tissue section is placed would have to be made porous with periodic holes if the substrate material (e.g., glass slide) is not intrinsically porous to gases.

A further embodiment involves entrapping molecules of interest in the thermoplastic polymer matrix in order to perform affinity purification on this solid matrix without dilution of the desired molecules. Affinity microbeads or nanoparticles can be added during a tissue section fixation/staining step. After specific microtransfer to the thermoplastic polymer, these affinity particles (e.g., hydrophobic G18 beads for lipids, beads that specifically bind polynucleotides or even specific polynucleotides such as mRNA) would be colocalized with the captured tissue in the polymer matrix allowing the retention within the matrix of only those macromolecules that specifically bond to the affinity particles during subsequent washings of the film with tissue dissolving solutions (e.g., typical proteinase K buffers for polyneucleotides or alkali extraction buffers for most molecular species). In this way after a simple tissue wash, the macromolecules of interest would be retained within the polymer matrix surface layer at roughly the same concentration that they existed within the specific cells in vivo. This purification without dilution of specific molecules to be analyzed within the specifically isolated cells, should make it practical to perform direct assays of the treated microtransfer films. Since these films are themselves transparent, this should enable quantitative and sensitive direct optical assays of multiple macromolecules within specific cell or organelle populations from complex tissues. Such integration of the microtransfer with downstream purification and analyses could provide tremendous benefits to cost, speed, and sensitivity. It may be possible in such cases, to perform complex multimolecular imaging within a tissue section satisfying the pathologists and researchers desire to study multiple complex macromolecular spatial profiles simultaneously.

The target activated transfer system 1 also optionally includes a scanner 20 and a computer monitor 21. Imaging of the samples for targeting is not required in this direct transfer process unlike other forms of tissue microdissection which use microscopes. This is because the distribution of stain in the specimen determines precisely where the light is absorbed (all tissue whether stained or not is exposed to a uniform light dose) and where the polymer melts and binds to the specifically stained regions. However a rapid lost cost flat-bed scanner is quite useful for archiving images of the tissue and transfer film before and after transfer and for more sophisticated forms or automated dosimetry and process control. In order to predetermine dosimetry and regions to be selective transferred, the stained tissue section may be imaged before transfer in the scanner 20. The scanned reference image may be displayed on the computer monitor 21. The scanner 20 may be a low cost flat bed color scanner with sufficient resolution and contrast sensitivity (e.g. 48-bit 3 color images) to allow automatic determination of OD variations within the tissue. However, any type of imaging system can be used to make the scanned reference image. Illustrative imaging systems include digital imaging systems such as CCD camera systems, a photomultiplier or an automated color film scanner. An image analysis system (for example, using image analysis software in conjunction with an image and/or dosimetry database) or a manual observation of the images may depict the type of staining, the variability of the staining with and between tissue regions or individual cells, determine the staining intensity qualitatively, semi-quantitatively (scale 0 to 4, for example) or in a full quantitative analysis of the staining reaction (gray scale values, for example from 1-256, or as a color/hue of the specimens). The imaging system could separately determine the staining reaction in different parts of the spot, such as separately in stromal or carcinoma components. A computer may be used to compare automatically the staining results between adjacent sections of the same tissue section with same or different antibodies to form ratios of molecular intensities. Another example of a scanning system that could be employed in the target activated transfer system is described in U.S. Patent Publication No. 2003-0215936-A1, which is incorporated herein by reference.

Scanner 20 permits unattended automatic scanning of prepared tissue sections for the detection of candidate objects of interest, such as particular cells which may contain marker identifying reagents, and evaluation of the amount of the reagent that is present. For instance, scanner 20 may automatically locate candidate objects of interest present in a biological specimen on the basis of color, size and shape characteristics.

An imaging system not only acquires images from a microscope slide, but may also archive, display, and analyze the images and incorporate data in a database. For example, the imaging system can display consecutive images on a computer screen for an observer to analyze, interpret and store. Alternatively, the program can pre-process images to display areas of positive staining, and present images of selected slides or specific regions of slides to the observer for approval. Completely automated image acquisition and analysis and microtransfer is possible.

In operation, a slide mounted with a tissue sample is placed into the scanner 20. The scanned image is stored in a computer. The slide and the film then are secured onto the x-y translating stage 3. The slide in the x-y translating stage 3 can then be registered with the scanned reference image (i.e., the image "roadmap") that may displayed on the computer monitor 21. The activation of the laser beam, the air-jet, and the x-y translating stage may be controlled by a computer. As mentioned above, registration of the film to the moving tissue section and tissue slide can be maintained by the air-bearing, surface tension of the film to the glass of the tissue slide, and/or the adhesive force of the initial bond between the film and the tissue section.

Air (via the air-jet) and the laser beam (via the optical assembly and the fiber optic cable) are directed towards the outer surface of the film. The air and the laser beam may be activated simultaneously to effect transfer bonding or only the air may be flowing through the nozzle if the proximal end of the irradiating mechanism is positioned over a region of the tissue sample that has not been targeted for tissue transfer. The locally melted layer of the thermoplastic film under the applied air pressure flows rapidly through the locally heated stained surface to fill the tissue immediately below the stained layer. The force of the air pressure applied by the air-jet is sufficient to maintain contact between the film surface and the tissue sample surface, but not so great as to damage the film and/or the tissue sample. For example, the applied air pressure may exert a substantially constant force of about 1 g/mm to about 10 g/mm$^2$, more particularly about 4 g/mm$^2$. The air pressure is locally applied for about 5 to about 200 milliseconds (typically ~30 milliseconds) before and after the laser passes a given point in the tissue. This enables reliable contact and impregnation of the specifically stained regions to occur within about 1 to about 3 milliseconds. An advantage of the rapid scan speed of the system and constant pressure on a flexible film is each stained point is only briefly heated so that the deposited heat is efficiently transferred to the 1 µm layer of the polymer surface in contact with it resulting in very local and efficient polymer melting and then incremental advancement due to the applied pressure of this thin layer into the underlying porous tissue.

After the laser beam moves away from the local spot, the locally-applied heat stops, and rapid cooling in ~1 millisecond causes the polymer to solidify within the stained target and tissue sublayer. When the underlying glass slide is reached by the advancing molten polymer the rapid increase in heat loss into the glass effectively quenches further polymer melting. After the scan of the whole tissue region is completed, the flexible film is peeled off the tissue slide, carrying with it the polymer impregnated stained tissue but leaving behind laterally adjacent regions (normal to the laser beam or z direction). This tape can be easily imaged by the flat bed scanner 20 to give an archival image of the 2D morphology of those cells that were captured.

The whole tissue is scanned with a uniform intensity/duration of light energy density (fluence), but only those regions that are strongly stained absorb sufficient energy to melt the thermoplastic film surface where it contacts the tissue, thereby automatically bonding only the tissue locations exceeding some threshold stain density. As no microscopic targeting decisions must be made by a viewer or computer analysis (as required in present laser microdisection techniques), the system can routinely bond more than 5000 specifically labelled cells per sec, which represents an increase of at least 1000-fold over conventional laser capture microdissection. In combination with a large laser beam (e.g., 120 microns in diameter) and rapid translation, the entire tissue section containing millions of cells and be scanned in on the order of 100 seconds. In one example, the high speed x-y translating stage 3 translates the tissue slide 11 in raster scan at speeds ranging from 10 to 80 mm/sec through a fixed 120 µm diameter laser beam meaning that 4 to 30 mm$^2$/sec of the tissue sample area can be scanned which approximates to about 20,000 cells/sec to about 150,000 cells/sec. By using target-specific tissue stains with a high OD (>0.5) at the specific laser wavelength used, this system is rather robust for variations in stain density as virtually the same amount of energy is locally deposited in the stained regions regardless of OD (when >0.5) and the small differences in thermal gradients are rapidly averaged by heat conduction in the advancing molten polymer. At lower local stain densities (<0.3 OD), the system allows for sequential isolation of cell targets of different stain density (e.g., molecular marker density) starting first with the most dense and on sequential transfer films those with progressively lower stain density as the light dosimetry (fluence) is gradually increased.

The measured local light transmission or optical density of the tissue slide pre-microtransfer image can then be related to microtransfer dosimetry (dependent on factors including stain absorption spectrum, laser wavelength used, tissue section thickness, and thermoplastic polymer used) in order to predict what regions will be transferred for any given dosimetry. In one aspect, a computer database may store dosimetry information for correlation with the scanned reference image. This feature is particularly useful when stain density among different sections varies or if the sample is to be selectively mined by first transferring only the most highly stained regions and then after removal of these targets, placing another film on the partially harvested tissue section and transferring less heavily stained cells (e.g., those with slightly lower targeted molecule expression levels). Similarly, it will be possible to use spectrally separated specific stains of different molecules and use two laser wavelengths to collect either two different cell populations or in a combined mode only those cells whose combined expression of two molecules exceeds a certain level. This method could allow mulitparameter cell isolation similar to the ability of a fluorescence activated cell sorter to isolate cells from single cell suspensions on the basis of the coincidence of multiple parameter windows (e.g co-expression of two marker macromolecules).

A roadmap image of the entire specimen can be rapidly generated at ~10 um resolution with a standard commercial flat bed scanner. However, as explained above, such scanning with an imaging system is not required in order to determine where the irradiation, and thus the microadhering, should be directed. The imaging system described herein is useful for modifying or optimizing the dosimetry and/or for image archiving. The system is designed to permit selection of specific larger regions of the tissue to be selectively scanned—for example a whole prostate section might be viewed but only the regions in which invasive carcinoma appears might be scanned onto one film and then regions of normal or premalignant lesions transferred onto a subsequent slide. Although this requires some general targeting decisions, the microscopic targeting would be automatically afforded by the cell specific absorptive stain. A similar example of this regional selection, would be to limit the laser scan to specific regions of the brain that are readily recognized by gross morphology (e.g., hypothalamus or a substructure like the supra-optic nucleus). Again specific stains would allow specific cell types or organelles to be collected from the selected macroscopic regions. Other methods of selecting regional samples based on morphology in addition to the molecularly specific stains include rapidly automatically scanning the whole slide and then cutting out specific regions from the transferred film based on the intact morphological structure preserved in the direct transfer process. Using affinity particle purification within the transfer film could allow in situ microscopic examination of the distribution of retained and subsequently labeled macromolecules.

The x-y plane resolution of transfer is determined by the spatial localization of the stain rather than the beam size or "pulse duration" as is the case in laser capture microdissection. The system can achieve tissue transfers with 1 µm lateral (x-y plane) resolution when using a 120 µm laser beam. We believe that it may be possible to achieve sub-diffraction limited microtransfers using our optical technology which makes practical the isolation of organelles and other specifically labeled subcellular elements. Thus this automated microtransfer is both more rapid than traditional laser microdissection and of much higher intrinsic resolution (a previously unexpected and unknown capability)—the target activated transfer system 1 uniquely offers this combination of speed and resolution over any previous approaches.

Any or all of the operation of the tissue transfer station may be controlled by a controller such as a computer. The controller may, for example, control movement of the x-y translating stage 3 by controlling the x drive and the y drive; control operation and alignment of irradiating assembly 5; control the flow of the air through the coaxial air-jet; and control the placement and movement of the tissue section. The computer may also perform analysis and comparison of the scanned image as described above.

EXAMPLE 21

Dye-Based Tissue Transfer

Frozen mouse tissue sections were incubated with Eosin Y (Sigma, Cat# E 4382), Janus Green (Sigma, Cat# J2125), Hematoxylin (Sigma, Cat# H3136), Bromophenol Blue (Bio-Rad, Cat# 161-0404), Coomassie Blue (Calbiochem, Cat# 234735), or Azure A (Sigma, Cat# A 6270) for 20 seconds at room temperature, then washed generously in diH$_2$O. Stains were prepared by combining 1 g of dye with 40 ml of diH$_2$O. Allowed to air dry and then dehydrated the tissue in graded alcohols and xylene. Using a clear EVA cap as the transfer substrate, lifted stained cells using a LCM laser with a power level of 100 mW and a pulse duration of 75 ms.

Immuno Histogold-Based Tissue Transfer

A frozen prostate tissue section was incubated with the Zymed Histogold Staining Kit (cat# 95-6549) with Mouse Anti-Cytokeratin AE1/AE3 as the primary antibody. Staining was good, incubated with last step for about 40 minutes to get very dark staining, some mild background. Dissected tissue via EVA cap transfer substrate with the LCM laser set on 100 mW power and 75 ms duration. Specific melting and lifting were achieved.

It will be apparent that the details of the methods described may be varied or modified without departing from the spirit of the described invention. The invention includes all such modifications and variations.

We claim:

1. A device for performing target activated transfer from a tissue sample in which a localized reagent specifically determines the microadhering of desired cellular material in the tissue sample, the device comprising:
    a mounting surface for mounting a tissue sample;
    a tissue sample mounted on the mounting surface, wherein the tissue sample is stained with the reagent that localizes specifically at targeted cellular material;
    a transfer surface positioned adjacent to the tissue sample, wherein the transfer surface has sufficient surface area to cover the entire tissue sample; and
    a light source positioned to substantially uniformly irradiate both stained and unstained regions of the tissue sample simultaneously with light energy that activates the reagent, wherein the activated reagent produces a change in the transfer surface and selectively adheres the stained regions to the transfer surface.

2. The device of claim 1, wherein the transfer surface comprises a transparent thermoplastic polymer and the device is configured so that a surface of the stained region is in precise contact with the transparent thermoplastic polymer.

3. The device of claim 1, wherein the light source is an immobile single light source that irradiates substantially the entire tissue sample in a single flash.

4. The device of claim 1, wherein the light source has a spectral output matched to the adsorption spectrum of the localized reagent.

5. The device of claim 1, wherein the amount of light energy is adjustable to selectively isolate different populations of the stained regions based on different densities of specific stained targets.

6. The device of claim 1, wherein the light source is a constant intensity light source that scans and irradiates across the tissue sample.

7. The device of claim 1, wherein the light source illuminates less than the entire mounting surface, and the mounting surface is movable to increase an area of the mounting surface that is illuminated by the light source.

8. The device of claim 7, wherein the mounting surface is movable in a predetermined pattern to illuminate the tissue sample mounted on the mounting surface.

9. The device of claim 1, wherein the tissue sample is covered with the transfer surface to which the targeted cellular material adheres after the light source irradiates the tissue sample on the mounting surface.

10. The device of claim 1, wherein the transfer surface is an inner surface of a flexible transfer film disposed above the tissue sample, and further comprising an irradiating assembly that includes an optical assembly that is optically coupled to the light source, the irradiating assembly having a proximal end; and a gas-bearing disposed between the proximal end of the irradiating assembly and an outer surface of the flexible transfer film and configured to generate a flow of gas between the outer surface of the flexible transfer film and the proximal end of the irradiating assembly.

11. The device of claim 10, wherein the irradiating assembly further includes a gas-jet configured to generate the gas-bearing.

12. The device of claim 1, further comprising means for directing gas against the transfer surface so that the transfer surface contacts the tissue sample.

13. The device of claim 1, wherein the device is configured so that a transparent transfer film can be placed into contact with the tissue sample.

14. The device of claim 1, wherein an imaging apparatus is not required to direct the microadhering of desired cellular material in the tissue sample.

15. An automated system for transferring tissue from a tissue sample to a transfer substrate, the system comprising:
    a tissue transfer station that includes an irradiating assembly, an x-y translating stage configured to translate a tissue slide upon which a tissue section can be mounted, and an air-bearing between the irradiating assembly and a transfer substrate that is positioned over the tissue sample; and
    a controller for controlling the position of the x-y translating stage,
    wherein the air-bearing comprises an air-jet configured to generate a flow of gas between the irradiating assembly and the transfer substrate and the air-bearing supports the irradiating assembly off of the transfer substrate.

16. The system of claim 15, further comprising a scanner and a monitor.

17. The system of claim 15, wherein the irradiating assembly includes a moveable optical assembly, and the air-bearing supports the moveable optical assembly so that a gap is maintained between the optical assembly and the transfer substrate.

18. The system of claim 15, wherein the moveable optical assembly is optically coupled to a light source.

19. The device of claim 1, wherein the reagent changes the target such that the target is capable of being selectively heated, and the transfer surface is activatable by heat from the target to adhere the target to the transfer surface.

20. The device of claim 19, wherein the reagent is an immunoreagent that carries an activating moiety that activates the transfer surface.

21. The device of claim 20, wherein the activating moiety comprises a moiety that absorbs electromagnetic radiation to produce heat.

22. The device of claim 21, wherein the moiety that absorbs electromagnetic radiation comprises a chromophore.

23. The device of claim 18, wherein the light source comprises a laser beam and the air-bearing comprises an air-jet, the air-jet being coaxial with the laser beam.

24. An automated system for transferring tissue from a tissue sample to a transfer substrate, the system comprising:
- a tissue transfer station that includes an irradiating assembly, an x-y translating stage configured to translate a tissue slide upon which a tissue section can be mounted, and means for generating a gas-bearing between the irradiating assembly and a transfer substrate that is positioned over the tissue sample; and
- a controller for controlling the position of the x-y translating stage, wherein the gas-bearing generates a flow of gas between the irradiating assembly and the transfer substrate and the gas-bearing supports the irradiating assembly off of the transfer substrate.

25. The system of claim 24, wherein the system does not include an imaging apparatus.

26. The system of claim 17, wherein the gap has a width of 1 to 2 µm.

27. The device of claim 14, wherein the light source comprises a laser.

28. The system of claim 25, wherein the irradiating assembly comprises a laser.

* * * * *